(12) United States Patent
Gandjbakhche et al.

(10) Patent No.: US 6,990,369 B2
(45) Date of Patent: Jan. 24, 2006

(54) PROBE USING DIFFUSE-REFLECTANCE SPECTROSCOPY

(75) Inventors: Amir H. Gandjbakhche, Potomac, MD (US); David W. Hattery, Washington, DC (US); Jim Mulshine, Bethesda, MD (US); Paul Smith, Annapolis, MD (US); Victor Chernomordik, Rockville, MD (US); Edward Wellner, Fairfax, VA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/105,180

(22) Filed: Apr. 13, 2005

(65) Prior Publication Data
US 2005/0203354 A1    Sep. 15, 2005

Related U.S. Application Data

(63) Continuation of application No. 09/972,700, filed on Oct. 5, 2001.

(60) Provisional application No. 60/238,600, filed on Oct. 6, 2000.

(51) Int. Cl.
*A61B 6/00*    (2006.01)
(52) U.S. Cl. ............. 600/477; 600/407; 600/413; 600/476; 600/478; 600/310; 356/303; 356/432; 250/459.1; 250/461.2
(58) Field of Classification Search ........... 600/407, 600/413, 476, 477, 478, 310; 356/303, 432; 250/459.1, 461.2
See application file for complete search history.

(56) References Cited

U.S. PATENT DOCUMENTS 4,582,067 A    4/1986 Silverstein et al.

(Continued)

OTHER PUBLICATIONS

Arai et al., Aug. 1999, *American Journal of Physiology*, 277(2):H683-H697 "Myocardial oxygenation in vivo: optical spectroscopy of cytoplasmic myoglobin and mitochondrial cytochromes."

(Continued)

*Primary Examiner*—Ali Imam
*Assistant Examiner*—William C. Jung
(74) *Attorney, Agent, or Firm*—Merchant & Gould P.C.

(57) ABSTRACT

The invention provides a device and method for monitoring inflammation of the epithelium. The device consists of a head region, a handle region and an optical bundle. At least two of the optical fibers in the bundle are utilized as a source of radiation, these two fibers are at two different angles from normal. At least one of the other optical fibers is utilized as a detector for the reflected radiation, or alternatively an image guide can be used as the detector. The device of the invention can be part of an external or internal system that can include a light source, the device, a multiplexer, a spectrometer, and a computer for data analysis. The method of the invention allows for the detection and monitoring of general inflammation of the oral epithelium. The inflammation of the epithelium can be detected or monitored to diagnose diseases of the oral epithelium, monitor such diseases, monitor treatment of such diseases, or pre-screen for and monitor preventative treatments of such diseases.

24 Claims, 19 Drawing Sheets

U.S. PATENT DOCUMENTS

| | | | |
|---|---|---|---|
| 4,760,840 A | 8/1988 | Fournier, Jr. et al. | |
| 4,770,185 A | 9/1988 | Silverstein et al. | |
| 4,821,116 A | 4/1989 | Nagasaki et al. | |
| 5,076,825 A | 12/1991 | Hayami et al. | |
| 5,421,337 A | 6/1995 | Richards-Kortum et al. | 600/477 |
| 5,431,158 A | 7/1995 | Tirotta | |
| 5,573,531 A | 11/1996 | Gregory | |
| 5,590,660 A | 1/1997 | MacAulay et al. | |
| 5,693,043 A * | 12/1997 | Kittrell et al. | 606/15 |
| 5,776,129 A | 7/1998 | Mersch | |
| 5,827,190 A | 10/1998 | Palcic et al. | |
| 5,833,683 A | 11/1998 | Fuller et al. | |
| 5,847,832 A | 12/1998 | Liskow et al. | |
| 5,881,195 A | 3/1999 | Walker | |
| 5,897,562 A | 4/1999 | Bolanos et al. | |
| 5,910,816 A | 6/1999 | Fontenot et al. | |
| 6,013,053 A | 1/2000 | Bower et al. | |
| 6,086,558 A | 7/2000 | Bower et al. | |
| 6,091,984 A * | 7/2000 | Perelman et al. | 600/476 |
| 6,095,982 A | 8/2000 | Richards-Kortum et al. | |
| 6,104,939 A | 8/2000 | Groner et al. | |
| 6,108,082 A | 8/2000 | Pettipiece et al. | |
| 6,537,211 B1 * | 3/2003 | Wang et al. | 600/178 |
| 6,571,118 B1 * | 5/2003 | Utzinger et al. | 600/476 |

OTHER PUBLICATIONS

Cui et al., Feb. 1992, *IEEE Transactions on Biomedical Engineering*, 39(2):194-201 "The Relationship of Surface Reflectance Measurements to Optical Properties of Layered Biological Media,"

Doornbos et al., Apr. 1999, *Physics in Medicine & Biology*, 44(4):967-981 "The determination of in vivo human tissue optical properties and absolute chromophore concentrations using spatially resolved steady-state diffuse reflectance spectroscopy."

Farrell et al., Jul./Aug. 1992, *Medical Physics*, 19(4):879-888 "A diffusion theory model of spatically resolved, steady-state diffuse reflectance for the noninvasive for the noninvasive determination of tissue optical properties in vivo."

Gandjbakhche et al., Aug. 1999, *American Journal of Physiology*, 277(2):H698-H704 "Visible-light photon migration through myocardium in vivo."

Wan et al., *Photochemistry and Photobiology*, 34:493-499 "Analytical Modeling for the Optical Properties of the Skin with in vitro and in vivo Applications."

Zeng et al., Feb. 1993, *Physics in Medicine & Biology*, 38(2):231-240 "A computerized autofluorescence and diffuse reflectance spectroanalyser system for in vivo skin studies."

* cited by examiner

PROBE USING DIFFUSE-REFLECTANCE SPECTROSCOPY

This application is a continuation of United States patent application Ser. No. 9/972,700, filed Oct. 5, 2001, which claims priority to U.S. Provisional Application Ser. No. 60/238,600, filed Oct. 6, 2000, the disclosures of which are incorporated in their entirety.

STATEMENT OF RIGHTS TO INVENTIONS MADE UNDER FEDERALLY SPONSORED RESEARCH DEVELOPMENT

This invention has been developed with the support of the Department of Health and Human Services. The Government of the United States of America has certain rights in the invention.

FIELD OF THE INVENTION

The invention generally relates to a device and method for use in quantifying and monitoring inflammation of the epithelium. More particularly, the invention relates to fiber optic probes useful in a method for determining inflammation of epithelium tissue, which is relevant in a number of fields, including but not limited to dentistry, general medicine and internal medicine.

BACKGROUND OF THE INVENTION

Diagnosis of mammalian oral health often focuses on the epithelium. The epithelium is the covering of internal and external surfaces of the body, including the lining of vessels and other small cavities. It is made up of cells that are joined by small amounts of cementing substances. Epithelium is classified into different types, based on the depth of the layers and the shape of the cells residing at the surface.

The oral epithelium has a base layer of progenitor cells that are constantly replicating. As the newly replicated cells are formed at the base, they push the overlying cells toward the upper epithelial surface. As these cells approach the surface, they are flattened, eventually detached from the surface and will slough off. A healthy oral epithelium has a thickness in the range of 50–150 $\mu$m.

The first clinical symptom of an unhealthy oral epithelium is inflammation. Inflammation of the oral epithelium may result from either an increased proliferation rate of progenitor cells, a decreased detachment rate from the upper surfaces of the oral epithelium, or a combination thereof. Inflamed cell populations, including inflamed oral epithelium regions, produce cytokines that can specifically stimulate growth of evolving cancer clones. Normal epithelium populations will also respond to the chronic presence of mitogenically active cytokines by increasing their rate of cell growth. This increased cell growth is called hyperplasia. Normal epithelial cell hyperplasia can thereby be a measure of the promotional environment of a cancer clone.

The general health of the oral epithelium can sometimes be determined by visual inspection. For a more thorough diagnosis however, the thickness of the epithelium should be quantified. In order to quantify the thickness, more advanced techniques, such as endoscopy must be used.

Endoscopy is the visual inspection of a cavity of the body by use of an endoscope. An endoscope is generally a highly flexible viewing instrument that may also be capable of diagnostic and therapeutic functions. Endoscopy is widely used to diagnose, monitor and treat a number of diseases and maladies of the digestive system. Many diseases of the human digestive tract can be diagnosed by visual appearance, for example tumors possess a characteristic salmon pink color. In practice, these factors combine to allow one procedure, endoscopy, to be a relatively simple, non-surgical diagnosis and monitoring tool of many digestive tract diseases.

Use of diagnostic scopes as clinical tools was greatly advanced by the development of fiber optics in the 1950s. The use of fiber optics in diagnostic scopes allowed better images to be recorded. It also allowed more organs to be viewed because of the flexibility that fiber optics brought to the instrument. The flexibility added by fiber optics also decreased the incidence of puncturing body tissue and organs that occurred more often with rigid scopes.

Diffuse reflectance spectroscopy is a technique that was developed for use in surface analysis of powdered organic and inorganic samples. The technique is based on the diffuse reflectance of radiation that occurs when it is directed onto a surface with a matte finish or a powdered sample. The reflected radiation penetrates the sample and interacts with it before the radiation emerges from the sample as a "reflection". While the radiation is in the sample, scattering occurs such that the diffusely reflected light emerges from the sample at all angles, as opposed to the one angle that would be observed if the scattering had not occurred.

Reflectance spectroscopy has been used previously in a clinical setting. For example, reflectance spectroscopy has been used to determine oxygen levels in the myocardium in vivo. For details of such uses see, for example, Arai, A. E., Myocardial oxygenation in vivo: optical spectroscopy of cytoplasmic myoglobin and mitochondrial cytochromes. *Heart Circ. Physiol.* 46: H683–H697, 1999; or Gandjbakhche, Visible-light photon migration through myocardium in vivo. *Heart Circ. Physiol.* 46: H698–H704, 1999.

The use of reflectance spectroscopy in the diagnosis of oral health problems would provide a noninvasive, simple and inexpensive manner of diagnosis. However, little has been done furthering the diagnosis of oral health problems using such techniques. Further, the early diagnosis of maladies, such as gum disease and oral cancer often reduces the need for painful, if not disfiguring medical intervention. Therefore, there is a need for devices and methods that utilize reflectance spectroscopy that could be used in the diagnosis of oral health problems.

SUMMARY OF THE INVENTION

The invention utilizes diffuse reflectance spectroscopy to create a method and device whereby the epithelium/stroma boundary can be located in vivo with little or no discomfort to a patient, and epithelium inflammation can be quantified and monitored.

The invention is used for quantifying and monitoring inflammation of the epithelium layer and includes an optical bundle, a handle region and a head region that can be pivoted. Preferably, the optical bundle is configured in such a way that some of the fibers are utilized as detectors and others, utilized as sources are at angles of less than about 60° from normal. More preferably, the device includes an image guide as the detector and two fibers at angles of about 0° and 45° from normal as the source.

The method of the invention allows quantification and monitoring of general epithelium inflammation. Preferably, the method utilizes reflected photon intensity to locate the boundary of epithelium and stroma within a patient's mouth.

More preferably, the method utilizes a ratio of photon intensity from sources at different angles to locate the epithelium/stroma boundary and compare it to a normal epithelium/stroma boundary location or a prior boundary location of the same patient. The method also allows the epithelium thickness to be quantified by comparing the results to standards.

DETAILED DESCRIPTION OF THE INVENTION

The device of the invention allows for non-invasive quantification and monitoring of epithelium inflammation. The device utilizes diffuse reflectance spectroscopy and the physical characteristics of the epithelium and stromal layers of the tissue.

Figure 1:
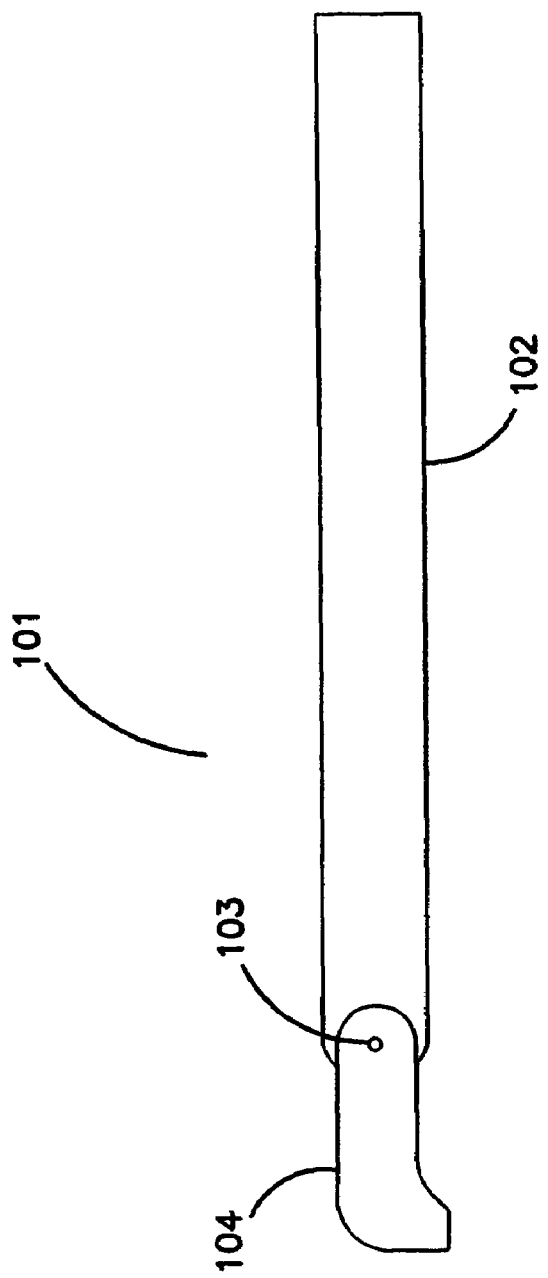
FIG. 1 is a plan view of an embodiment of a device of the invention.
Figure 2:
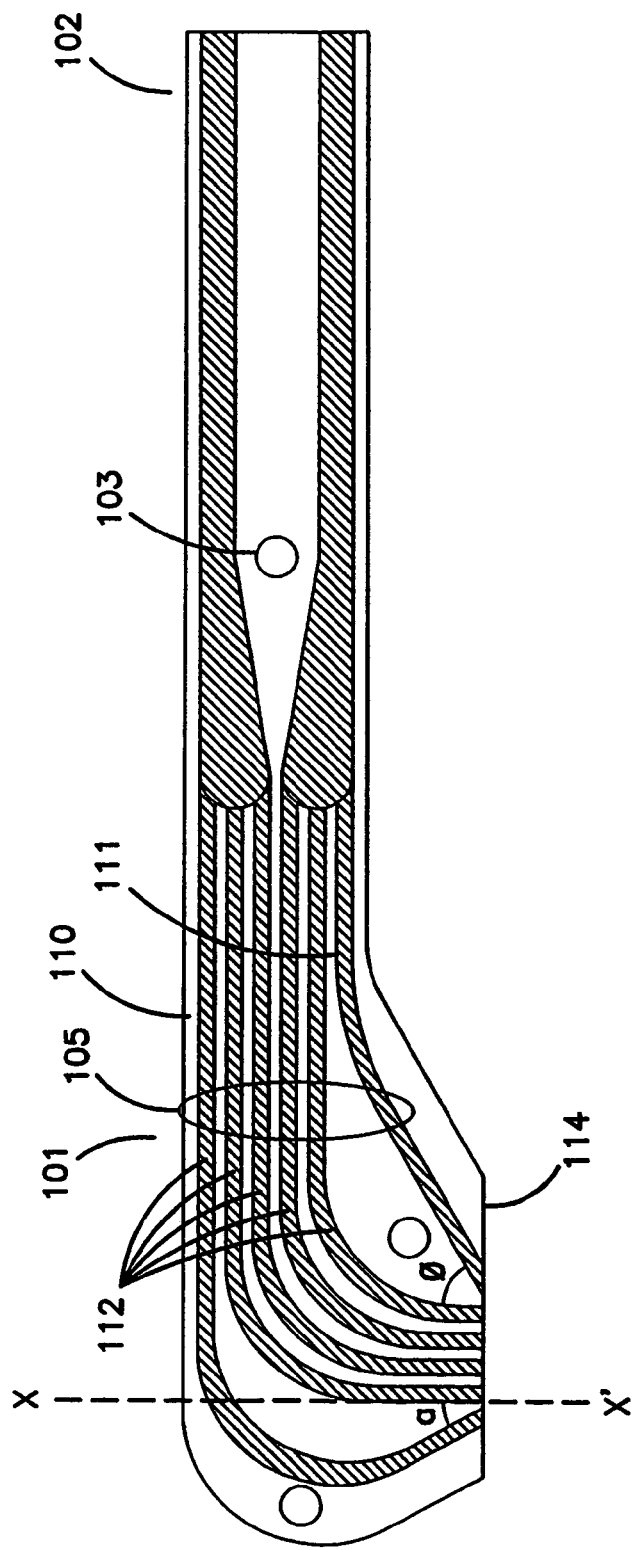
FIG. 2 is a cross sectional view of a side elevation of an embodiment of a device of the invention.

The device 101 includes a handle region 102, a head region 104 and an enclosed optical bundle 105 (FIG. 2). FIG. 1 depicts one example of a physical configuration of the device 101.

The handle region 102 allows the user to employ and manipulate the device 101. The handle region 102 can be made of any suitable material, including for example plastic or epoxy. Handle region 102 is generally configured so that the optical bundle portion of the device can be contained therein. Handle region 102 is preferably configured so as to be easily and comfortably manipulated by the user. Preferably, handle region 102 is made of plastic.

The handle region 102 is preferably connected to the head region 104 by a hinge assembly 103. The hinge assembly 103 is configured so that the head region 104 can be easily pivoted to allow correct and comfortable placement of the device 101 within the patient's mouth. The hinge assembly 103 is generally configured to allow the enclosed optical bundle 105 (shown in FIG. 2) to pass from the handle region 102 to the head region 104 without interference from the hinge assembly 103. Hinge assembly 103 can offer from 10 to 150 degrees of rotation. Hinge assembly 103 can be made of any acceptable material, including but not limited to plastic or stainless steel spring. Preferably, hinge assembly 103 is a stainless steel spring, and offers about 120 degrees of rotation.

The head region 104 houses the optical bundle 105. Head region 104 is also configured to provide the area of contact between the device 101 and the patient. Generally, head region 104 is configured so that it is comfortable and easily maneuvered within a patient's mouth. The head region 104 is configured so that the optical bundle 105 ends at the open end of the head region 104. Head region 104 can be constructed of any suitable material, including but not limited to plastic or epoxy. Preferably, head region 104 is made of plastic.

A device of the invention also includes an optical bundle 105. The purpose of the optical bundle 105 is two fold. The optical bundle 105 functions as the source of the light and the detector for the ultimate signal from the patient. Optical bundle 105 can be configured so that the individual fibers function as a source, as a detector, or as both a source and a detector. One embodiment of optical bundle 105 includes first source fiber 110, second source fiber 111, and detector fibers 112. The optical bundle 105 is constructed in such a way, and of acceptable materials so it can be enclosed by the handle region 102 and head region 104. At the distal end of the handle region 102, the optical bundle 105 is configured so as to allow connection to both the light source and the data collection and analysis system.

An example of an embodiment of an optical bundle 105 is depicted in FIG. 2. The optical bundle 105 is made up of individual optical fibers. In the optical bundle 105, some of the fibers are dedicated source fibers, while others are dedicated detector fibers. In the embodiment depicted in FIG. 2, first source fiber 110 and second source fiber 111 are configured as sources of radiation. Embodiments of the invention generally have at least two fibers as sources. The fibers configured as sources generally have two different angles, that is a first angle and a second angle from normal. Devices of the invention are configured with at least one fiber as a detector, or alternatively have another type of detector, such as an image conduit.

In one embodiment of the invention, first and second source fibers 110 and 111 have angles from about 0° to 60° from the normal. In this instance, normal is the axis X–X' which is at an angle of 90° from the contact area 114. As can be seen, the optical fibers may be normal to the contact area 114 in the space adjacent the contact area 114. Preferably optical bundle 105 is configured with first source fiber 110 having a 30° angle (a, FIG. 2) and second source fiber 111 having a 60° angle ($\phi$, FIG. 2) from the normal as defined by the detector fibers.

In one embodiment, the fibers of optical bundle 105 are polymer based fibers. Polymer based fibers allow the contact area 114 to be polished to create the angles necessary in first and second source fibers 110 and 111.

Figure 3:
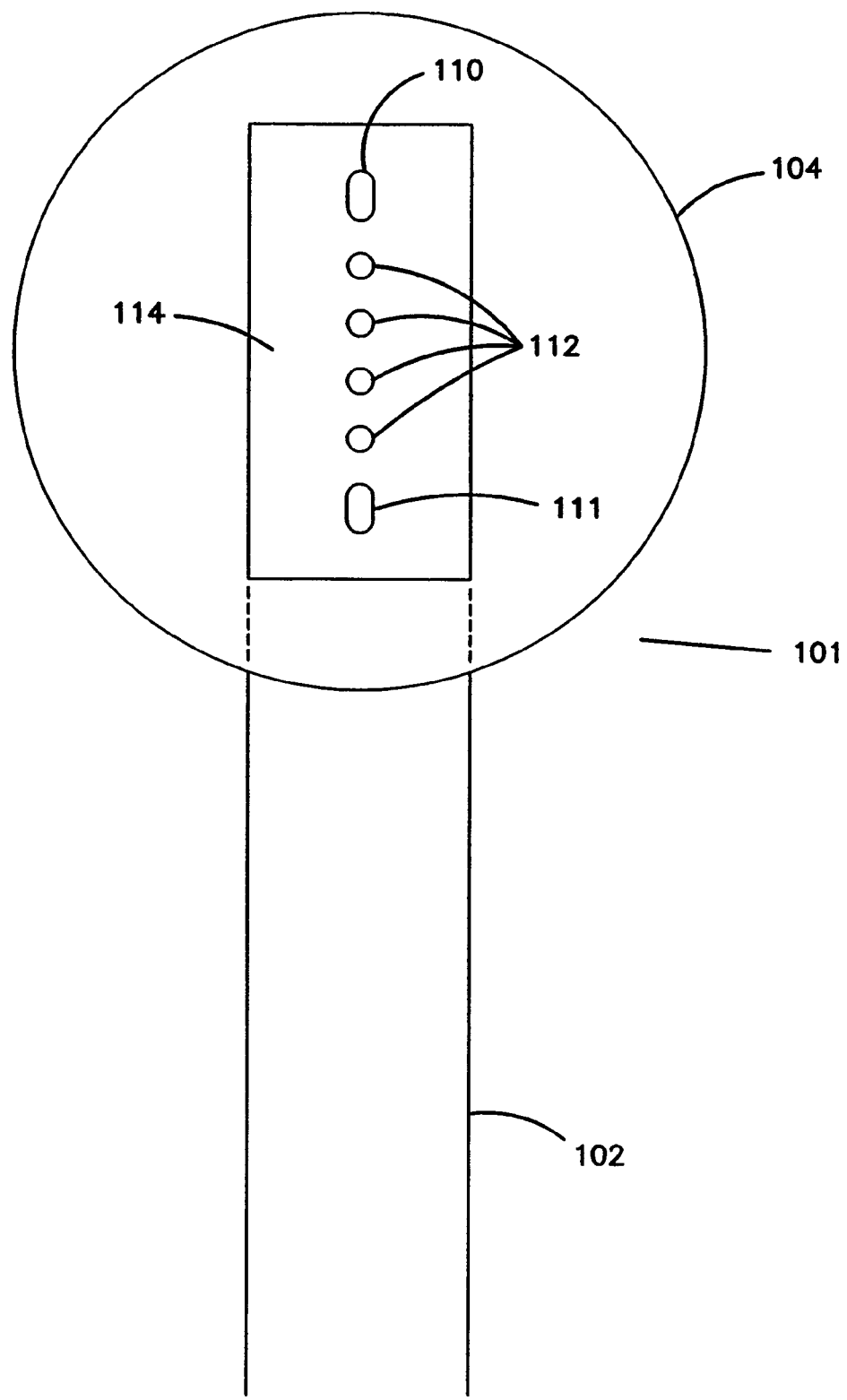
FIG. 3 depicts a bottom plan view of the head region of the embodiment of the invention shown in FIG. 2, from the bottom of the head region of the device.

FIG. 3 depicts a view of this embodiment of the invention from the perspective of the bottom of the head region 104. This view shows the vertical arrangement of the optical fibers of the optical bundle 105. The first and second source fibers 110 and 111 are oval in shape because they are polished in a plane defined by contact area 114 to create the desired angles.

Figure 4:
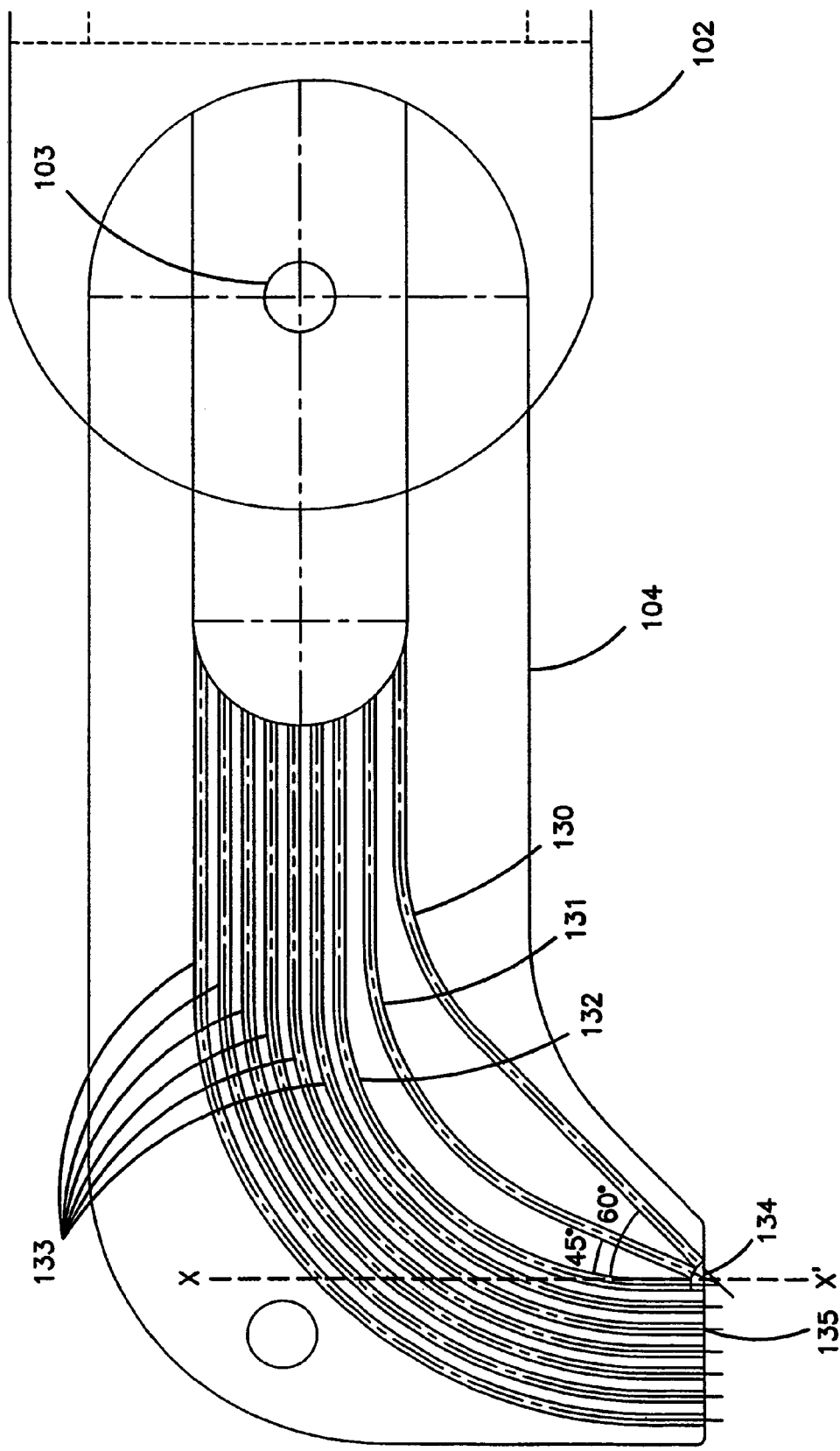
FIG. 4 is a cross sectional view of a side elevation of a further embodiment of the device of the invention.

Another embodiment of the device 101 of the invention is depicted in FIG. 4. First, second and third optical fibers 130, 131 and 132 are the source of the light for the device 101. Detector fibers 133 function to detect the intensity of the light reflected back from the sample being tested. The first, second and third optical fibers 130, 131 and 132 have angles of about 60°, 45° and 0°, respectively, from normal. The first, second and third optical fibers 130, 131 and 132 are preferably joined together to create the above angles by a transparent optical epoxy in the contact region 134. An example of suitable epoxies includes Norland optical adhesives, part nos.: 61, 63 or 6801 (Norland Optical Inc., New Brunswick N.J. 08902). The use of optical epoxy obviates the need for polishing the fibers to achieve the desired angles. Therefore, the fibers in this embodiment need not be polymer based, and virtually any type of optical fibers can be utilized.

Figure 5:
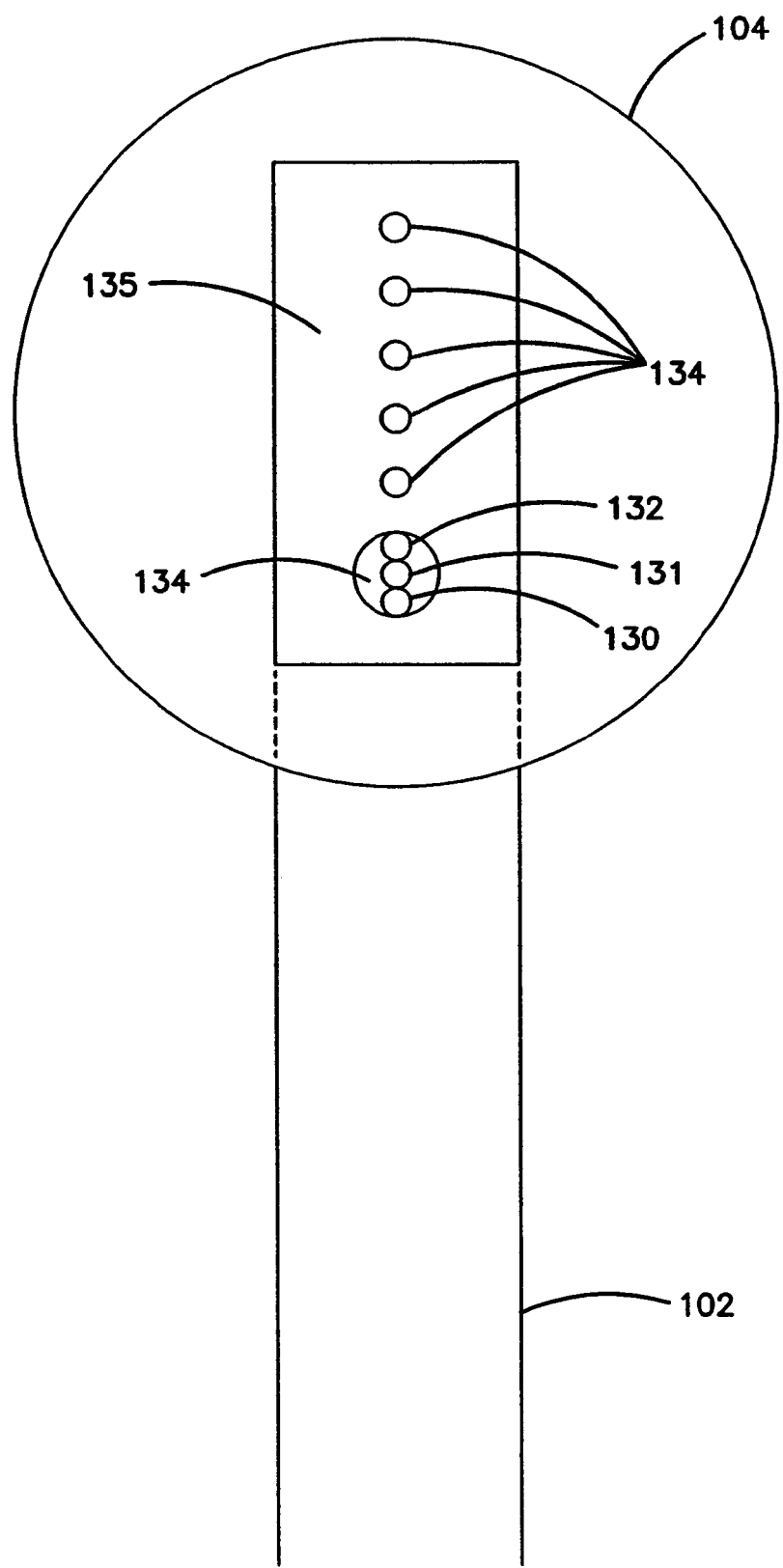
FIG. 5 depicts a bottom plan view of the head region of the embodiment of the invention shown in FIG. 4 from the bottom of the head region of the device.

FIG. 5 depicts a plan view of this embodiment of the invention from the perspective of the bottom of the head region 104. This view shows the vertical arrangement of the optical fibers of the optical bundle 105. The first, second and third source fibers 130, 131 and 132 are encased in transparent optical epoxy to maintain the desired angles.

Generally, the device utilizes two source fibers 130 and 131. The third source fiber 132, in this embodiment provides a third angle for use in analysis of the epithelium stroma boundary. As one will understand, having this specification, this third source provides further data for use in diagnosis of epithelial maladies.

Figure 6:
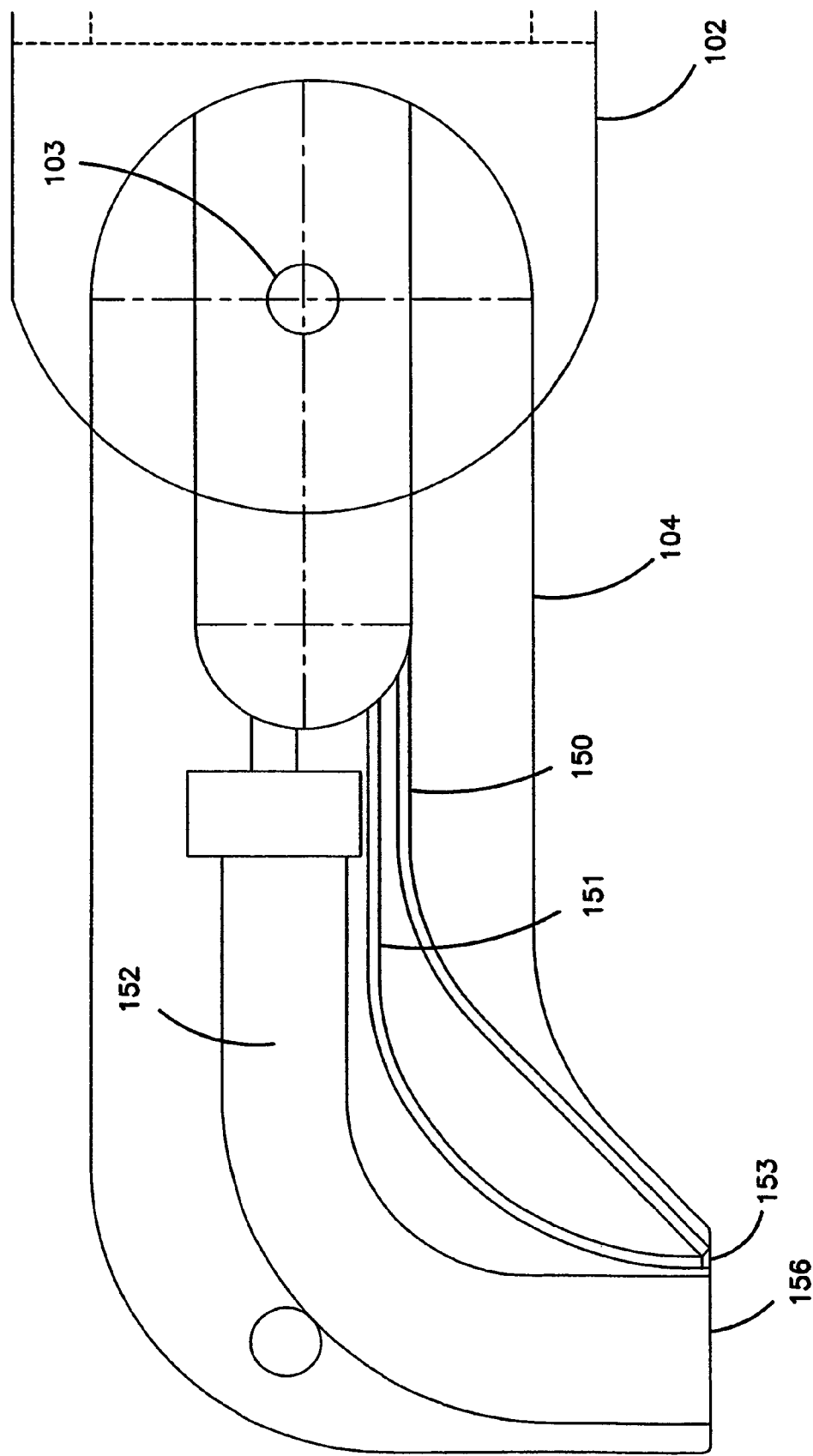
FIG. 6 is a cross sectional view of a side elevation of a further alternative embodiment of a device of the invention.

FIG. 6 depicts yet another embodiment of the invention. First and second optical source fibers 150 and 151 are the source of the light for this device. First and second optical source fibers 150 and 151 form angles of about 0° and 45° from normal. The first and second optical source fibers 150 and 151 are again joined by a transparent optical epoxy in the contact region 134. The image guide 152 functions as the detector for this embodiment of the invention. Specific image conduits that may be utilized in this specific embodiment include for example, high resolution fiber image conduit with fused glass rods–12 $\mu$m resolution, 305 mm in length with a 3.2 mm total diameter (Edmund Industrial Optics Catalog N997A pg. 207 stock # J38-302) and high resolution fiber image conduit with fused glass rods –24 $\mu$m resolution, 305 mm in length with a 6.4 mm total diameter (Edmund Industrial Optics Catalog N997A pg. 207 stock # J38-304). The image conduit 152 can be connected to a charge coupled device (CCD) camera (not shown).

Figure 7:
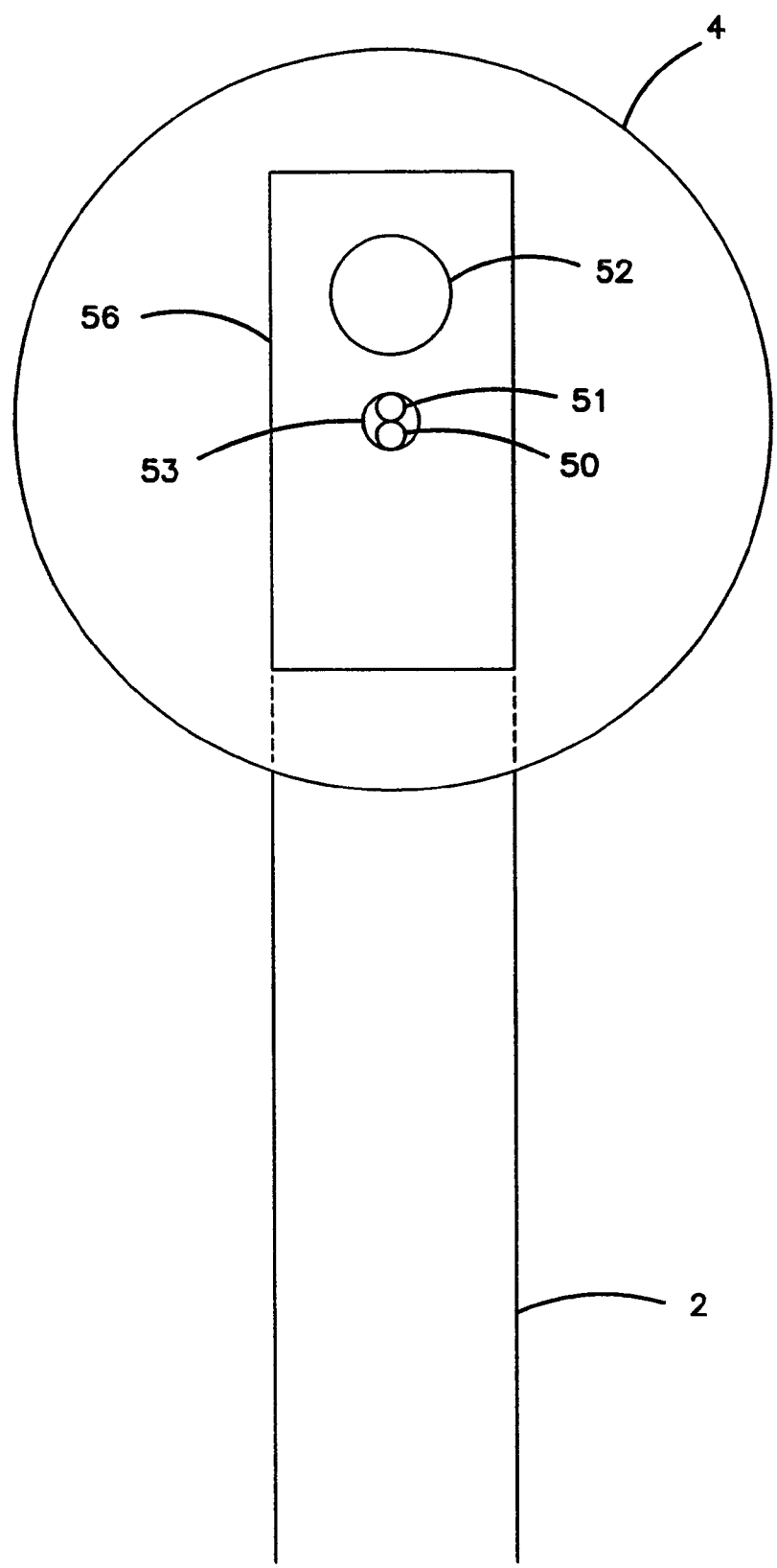
FIG. 7 depicts a bottom plan view of the head region of the embodiment of the invention shown in FIG. 4 from the bottom of the head region of the device.

FIG. 7 depicts a plan view of this embodiment of the invention from the perspective of the bottom of the head region 104. This view shows the vertical arrangement of the optical fibers and the image guide 152 of the optical bundle 105. The first and second optical source fibers 150 and 151 are encased in the transparent optical epoxy at contact region 134 in order to maintain the desired angles.

Figure 8:
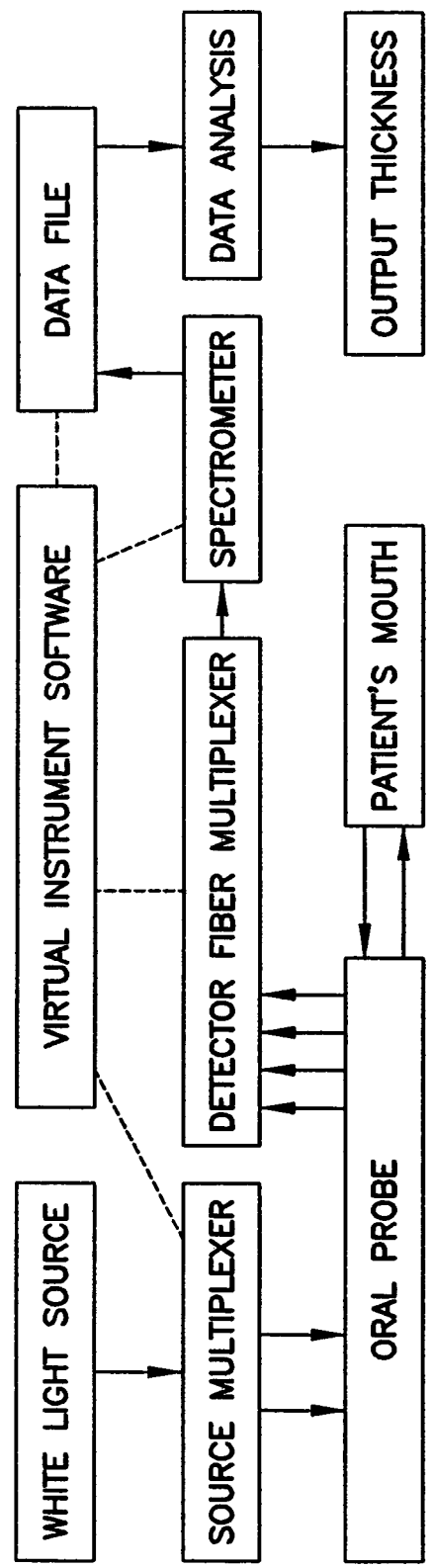
FIG. 8 is a block diagram illustrating a path that light takes in the oral diffuse-reflectance spectroscopy process.

Previous embodiments that were discussed can be used as part of a system in order to produce a signal, collect the data, and analyze the data. FIG. 8 is a block diagram illustrating a possible configuration of such a system, and how the device is used within a method of the invention.

A system utilizing a device of the invention, as illustrated in FIG. 8 contains a white light source, connected to a source multiplexer. The source multiplexer transmits the source energy to a device of the invention referred to in FIG. 8 as "oral probe". The oral probe then transmits light into the patient's mouth. Some of the light transmitted into the patient's mouth is reflected back and is received by the oral probe. This energy is then transmitted to a detector fiber multiplexer and then to a spectrometer which detects and measures the amount of light. The measurement of the amount of light is then saved into a data file. This data file is subjected to data analysis to output the thickness of the epithelium within the region of the patient's mouth that was subjected to the oral probe. Alternatively, the source multiplexer, the detector fiber multiplexer, the spectrometer, and the data file can all be controlled by a single system of software. In yet another alternative, the data analysis and output can also be controlled by the same software, or can be processed by another system. The invention includes embodiments of the device that contain elements capable of carrying out functions of other portions of the system, such as for example, components that produce a signal and collect data.

One example of a more self-contained device in accordance with the invention comprises a laser. Preferably the laser comprises a green HeNe laser or an orange HeNe laser. Embodiments with self-contained light sources obviate the need for a spectrometer to be part of the system. A multiplexer may be used in the self-contained device to switch from one light source to the other. A self-contained device could further be equipped with a microprocessor in order to carry out the data collection, data storage and data analysis steps.

Devices of the invention may also include optical fibers configured so that the absorption and scattering characteristics of the epithelium and stroma layer can be utilized to monitor epithelium inflammation. This includes the illustrated embodiments above with different types or varieties of optical fibers. It also includes devices constructed by using image guides as detectors. It further contemplates similar advances in radiation detection methods.

Methods of the invention are based on the physical differences between the epithelium and stroma layers. In one embodiment of the invention, a device of the invention is utilized. The device of the invention shines light from at least two different angles onto the area of interest. The device of the invention then detects the intensity of the reflected radiation at increasing distances from the source fibers. The log of the ratio of the intensities from the two different wavelengths is graphed versus the detector distance.

Graphs produced from this process are then used to locate the epithelium/stroma boundary. The boundary is detected by noting the point at which the slope of the line shifts. This slope shift can then be utilized in one of three different ways.

A line from the graph of the intensity ratio versus detector distance of a single patient can be monitored over time to detect any shift in the epithelium/stroma boundary. This shift could show either more or less epithelial inflammation.

Alternatively, the intensity ratio versus distance line of a single patient can be compared to theorized lines of differing epithelium thickness to get a qualitative measurement of epithelium thickness. The epithelium layer can then be given a definite thickness which could allow comparison to normal thickness. Alternatively, it could allow monitoring of the epithelium thickness over time.

Yet another alternative allows the intensity ratio versus distance line of a single patient to be compared to an intensity ratio versus distance line for a normal patient. This comparison can be used as a pre-screening technique. One use of this technique would be to detect patients with a risk of developing oral cancers and thereby locate candidates for chemo-preventative treatments. The patient's intensity ratio versus distance line could then be utilized further to monitor the chemo-preventative treatment and the further risk of development of oral cancers.

The method of the invention also contemplates other methods of calculating the epithelium/stroma boundary. The invention further contemplates other methods of determining epithelium thickness by utilizing the different absorption and scattering characteristics of the epithelium and stroma. The method also includes monitoring and detection of epithelium inflammation in other regions of the digestive tract. The method of monitoring epithelium inflammation can be used to monitor oral lesions, oral cancers and chemotherapeutic treatments and can also be used as a prescreening technique for disease and cancers that afflict the epithelium tissues.

WORKING EXAMPLES

The following examples provide nonlimiting illustrations of the device and methods of the invention.

Working Example #1

Leukoplakia are highly localized, firmly attached, thick white patches found on the tongue or other mucous membranes. They often occur as pre-cancerous growths. Leukoplakia on the oral epithelium is thought to develop in response to chronic irritation. Common causes of such chronic irritation are badly fitting dentures, smoking cigarettes, or chewing tobacco.

Leukoplakia is often visually diagnosed by a physician upon a routine examination of the mouth. Leukoplakia is the most common oral lesion worldwide. In a study of 23,616 white U.S. adults (97% white) who were over 35 years of age, 1.45% had leukoplakia. The prevalence is higher in males, with 2.81% of males having leukoplakia. Dental Abstracts, vol. 32, p. 423, 1987. Biopsies done on leukoplakia show a prominent thickening of the epithelial layer; from a normal 10–20 $\mu$m (average of three to five cell layers) up to approximately 100 $\mu$m (with corresponding proliferation of cell layers).

It seems highly likely that there is a connection between leukoplakia and oral cancer because virtually all patients that have oral cancer also have leukoplakia. Oral cancer is the sixth most common malignancy worldwide for individuals over the age of 35. Approximately 3% of patients with precursors of oral cancers have the afflicted region of the oral epithelium surgically removed. Oral cancers that directly follow leukoplakia are treated by surgically removing the afflicted region 0.03% of the time.

A randomized, double blind, placebo controlled, Phase 118 trial of Ketorolac mouth rinse on oropharyngeal leukoplakia was performed. Cyclooxygenase (Cox) inhibition leads to a decrease in PGE2 levels, as it is an enzyme necessary in the biosynthesic pathway. Since an increase in PGE2 and Cox-2 levels are associated with immunosuppression and carcinogenesis, a reduction in Cox-2 may be beneficial in arresting cancer development. This trial was aimed at evaluating the effect of reducing the inflammation of the oral epithelium by Ketorolac, and assessing its favorable effect upon the development of leukoplakia (and perhaps oral cancers). The inflammation in the epithelial layer over a three-month period was monitored using three different methods: an invasive punch biopsy and immunohistochemistry, optical coherence tomography (OCT), and a method and device of the invention.

The absorption of photons in a particular type of tissue was characterized, and a coefficient determined. The scattering of photons in that same tissue was characterized and a coefficient determined. When light was directed toward the epithelium, more light was scattered by the overlying epithelial layer than is scattered by the underlying stroma. Consequently, absorption was higher in the stroma than it is in the epithelium layer. This was due to a higher presence of hemoglobin in the stroma. The invention took advantage of these differences in scattering and absorption between the epithelium and the stroma in order to locate the boundary between the two layers.

In order to provide better depth resolution, two or more oblique angles were utilized. Further, in order to ensure that measurement was localized in the surface of the tissue, wavelengths of light that are more absorbed at the surface are utilized. High absorption at the surface also allowed use of a single scattering model of photon transport in the tissue, which simplifies the calculations.

Our assessment technique utilized optical reflectance spectroscopy (ORS), specifically oblique angle reflectance spectroscopy, in a time-efficient and non-invasive manner. Since the epithelium and stroma have different scattering ($\mu_s$) and absorption ($\mu_a$) properties (specifically the stroma has a greater concentration of hemoglobin due to increased vascularization) analysis of the decrease in photon intensity as the distance of the detector increases allowed; 1.) the boundary between the two layers to be found; and 2.) the quantification of tissue thickness.

The thickness of the epithelium layers was quantified by using known thicknesses of epithelium layers to produce an array of standard curves. Monitoring of both the boundary and the thickness over time allows for an assessment of the efficacy of a treatment protocol.

A theory that would predict the location of the epithelium/stroma boundary was also developed. Simulations based on a two-layer single scattering model have shown that a graph of the log of $$\frac{\text{photon intensity from a } 60° \text{ source}}{\text{photon intensity from a } 30° \text{ source}}$$

exhibits transitions from one slope to a lower slope (breakpoints) which correspond to the photons going out of the epithelial layer and into the stroma. This observed breakpoint represents the distance at which the boundary between the two layers occurs. Ultimately this is the point that should be monitored in patients. Additionally the value of the logarithmic ratio appears to be on the order of 0–5. An output for one such simulation is shown in FIG. 9.

Figure 9:
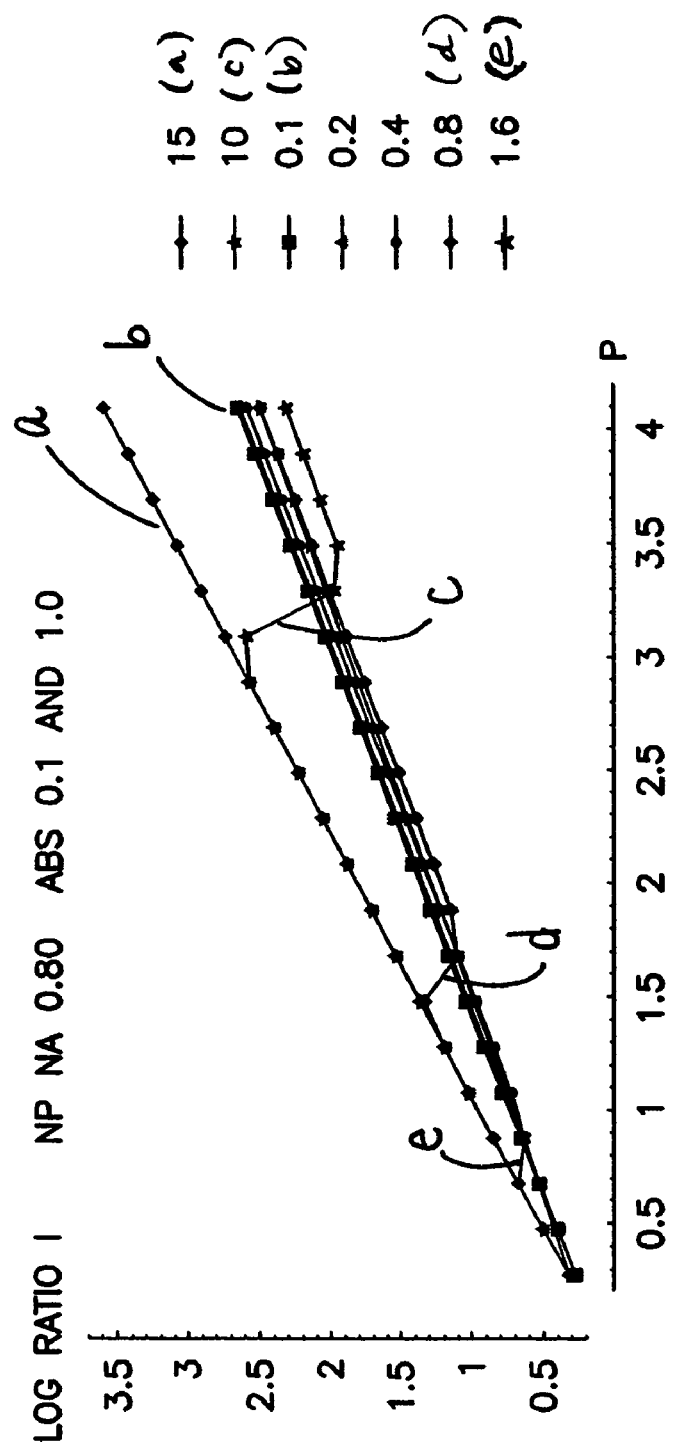
FIG. 9 is a graph that illustrates the detection of the epithelium/stroma boundary and illustrates standard graphs that allow quantification of epithelium thickness.

FIG. 9 is a theoretical plot that allows epithelium thickness to be quantified. Line a and b represent the epithelium and stroma respectively. Lines a and b represent graphs of scattering coefficients of 15 and 0.1, and are chosen because they are representative of the scattering in the epithelium and stroma respectively.

The remaining lines represent two layer systems of material scattering with a coefficient of 15 and 0.1 (epithelium and stroma respectively). The two layer systems represent different thicknesses. The lines c, d, and e have slope shifts which represent the boundary between the layer representing epithelium and the layer representing stroma.

By utilizing this theoretical plot, the thickness of an unknown epithelium layer can be predicted. The resolution of epithelium thickness is limited only by the number and spacing of the detector fibers or the resolution of the imaging guide.

Figure 10:
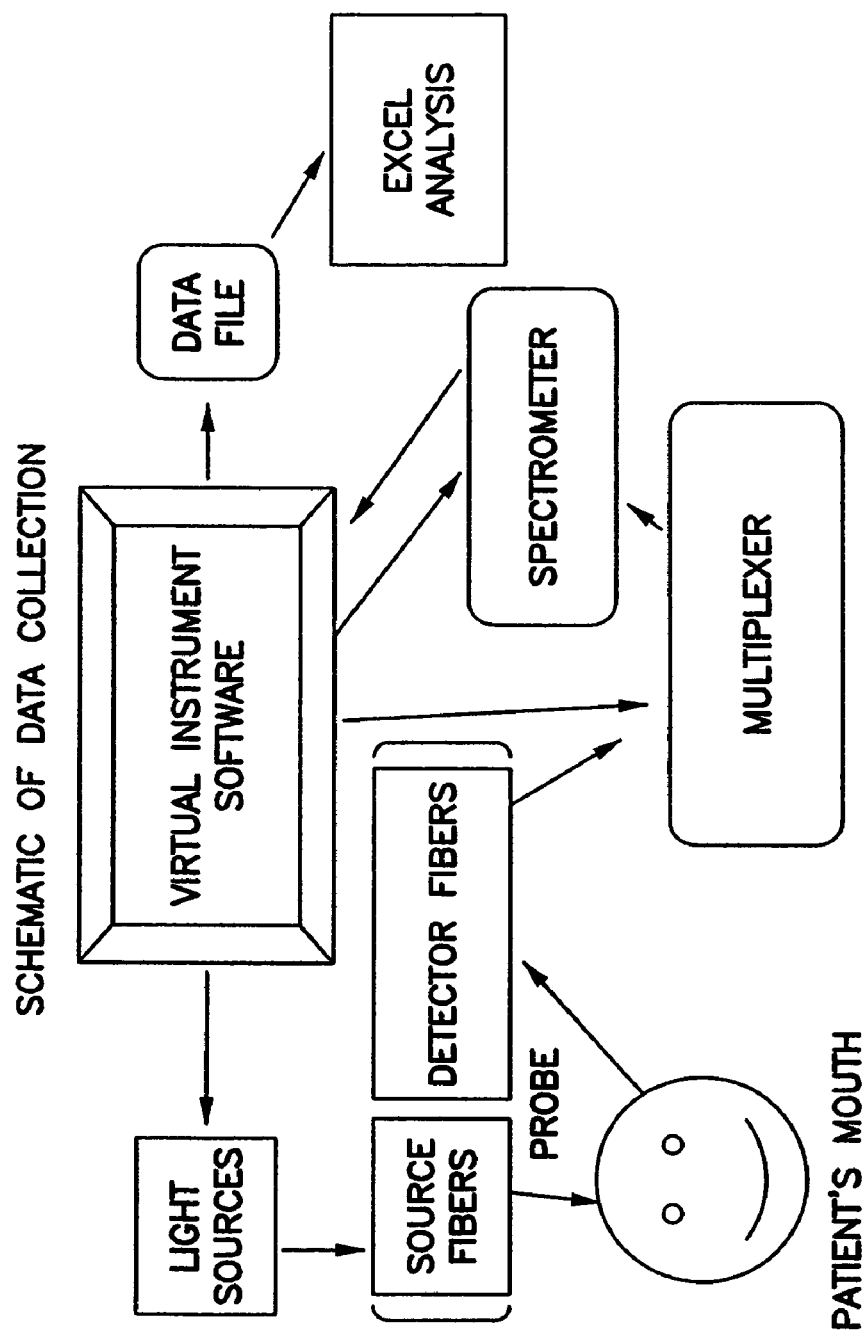
FIG. 10 is a schematic representation of a device of the invention as it could be configured to be part of a system for collecting data from a patient and analyzing it.

Materials and Methods for Data Collection:

The instrumentation used in the spectra collection included a device of the invention, configured as a fiber optic probe, a Fiber Optics Multiplexer, an Ocean Optics Spectrometer, National Instruments LabView Software and a Dell Computers Laptop. The analysis was performed using Microsoft Excel. A schematic of the data collection is shown in FIG. 10.

The probe was placed on a specific site in the patient's oral cavity and the Virtual Instrument (VI) program, written using LabView, was initiated. The program switched between the two light sources and controlled the multiplexer, which in turn switched between the four detector fibers. The spectrometer was also controlled by the VI program and recorded the spectra from each detector-source combination and sent it to the VI program to be recorded. The VI program would record the spectra as a data file and this data file was input into Microsoft Excel for analysis.

Various sites within the oral cavity were analyzed, in particular the bilateral lower lip, bilateral buccal mucosa, and an observable leukoplakia lesion. Four individuals were tested; a nineteen year old non-smoking adult male (used as a control), and three elderly males with a positive history of leukoplakia who presented with observable oral leukoplakia lesions.

Data Analysis:

The spectra recorded in the data collection process were saved as data files. Each file contained eight arrays. Each array represented the photon intensity across various wavelengths for a specific source-detector pairing.

Since the difference between the optical properties of the epithelial and stromal layers is due mainly to the higher concentration of hemoglobin in the stroma, wavelengths where the hemoglobin absorption peaks lay were utilized. These peaks occur between 500 and 600 nanometers. After the spectral data was collected, it had to be corrected based on four factors.

1) Dark Count—In the absence of a light source the spectrometer still showed a photon count. This count increased with time and was a function of wavelength. Thus the spectra were adjusted for this "Dark Count," so that the readings were only due to the light source. The Dark Count was modeled to a two-parameter function, F(A, t), and subtracted from the input spectra.

2) Light source intensity—The two light sources that supplied the 30° and 60° source fibers had different output intensities. A linear scaling factor was applied to the data to account for this difference.

3) Collection Efficiency of Detector Fibers—Each detector fiber (2-5) varied in its ability to detect photons, therefore normalization factors were applied to the data according to collection efficiency of each fiber.

4) Distance from source to detector—the configuration of the device led to a difference in the source to detector spacing, since the number of photons detected by the detector decreases exponentially with distance, a logarithmic and linear calibration factor was applied.

The adjusted data was then analyzed in two manners. First, the logarithmic ratio of the 60° to the 30° source photon drop-off with distance was graphed for each site. The purpose of this was to characterize the photon path and to determine if a breakpoint was seen, as was predicted by the theoretical calculations discussed above. Second, the ratio of the previous graph with respect to number of photons seen at the first detector to the number of photons at the last detector across various wavelengths was plotted. This graph was constructed to monitor the degree of inflammation across the different sites monitored.

Preliminary Findings & Conclusions:

Analysis of the first patient's spectra revealed discrepancies in the results. These discrepancies were due to insufficient intensity at the greatest source-detector distance. Quantification of this data was not performed.

In regards to patients 2 and 3, a lower initial to final intensity (detector 1/detector 4) ratio of the two sources was observed when compared to the control. Table 1 below relates the ratio values.

TABLE 1

| Site | Control Adult Male | Patient 2 | Patient 3 |
|---|---|---|---|
| Lower Lip | 1.49–1.83 | 0.90–1.3 | 0.68–0.95 (left lip only) |
| Buccal Mucosa | 1.13–1.24 | 0.98–1.06 (left side only) | 0.78–1.02 |

This depressed ratio in the patients with a history of leukoplakia relates to the photon migration difference due to an inflamed epithelium as compared with a normal non-inflamed epithelium. Further analysis of this observed difference can be performed to quantify the epithelial thickness.

Figure 11:
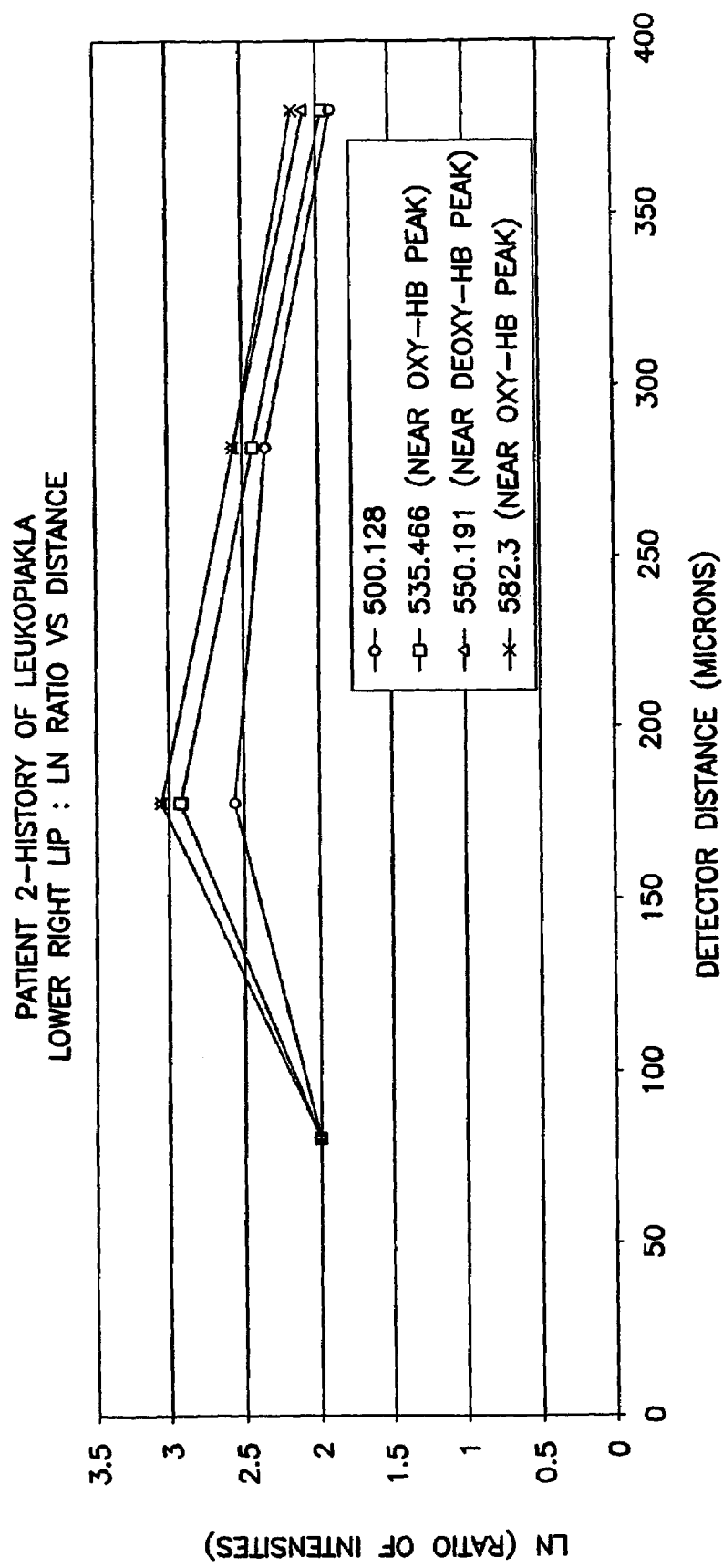
FIG. 11 is a graph that shows data collected, using a device and method of the invention, from the lip of a patient with a history of leukoplakia.
Figure 12:
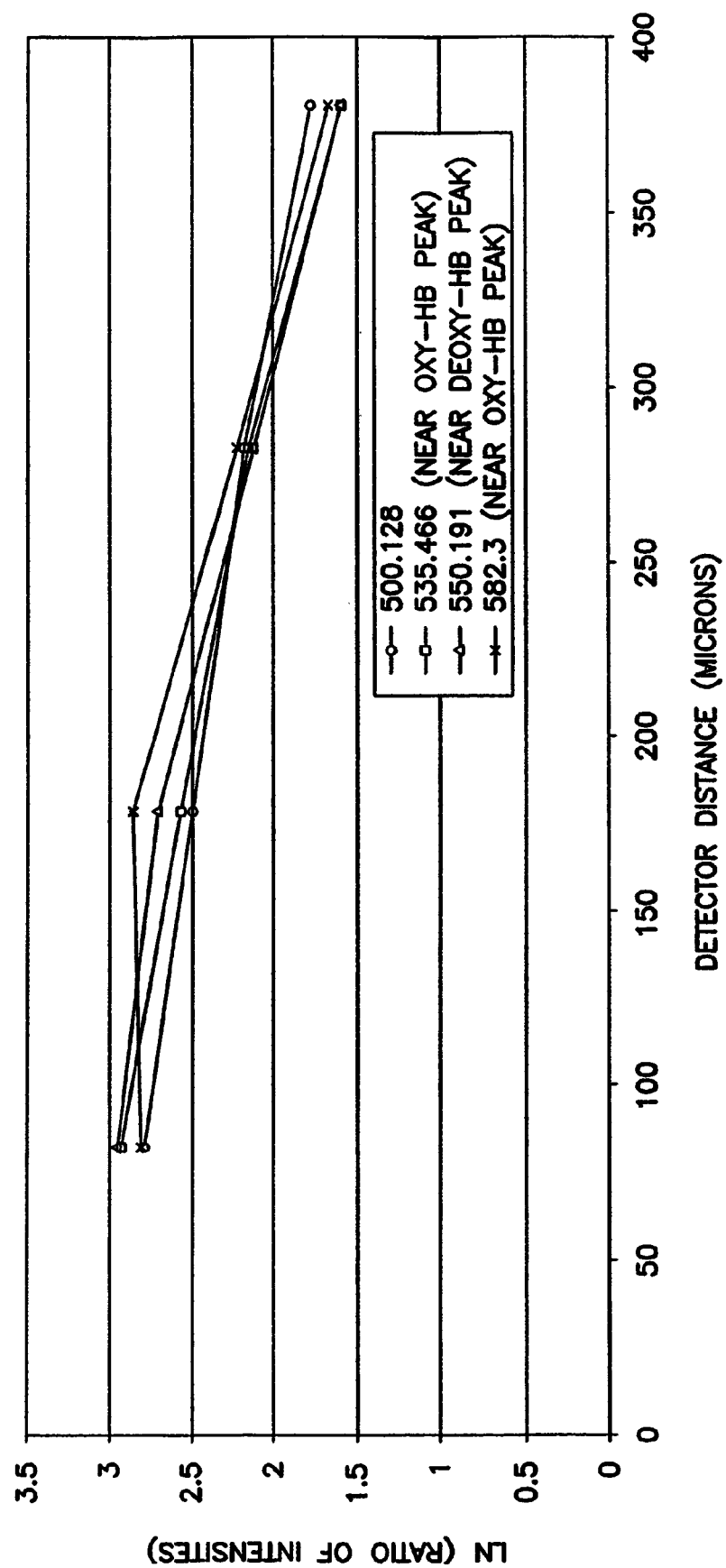
FIG. 12 is a graph that shows data collected, using a device and method of the invention, from the lip of a normal patient.
Figure 13:
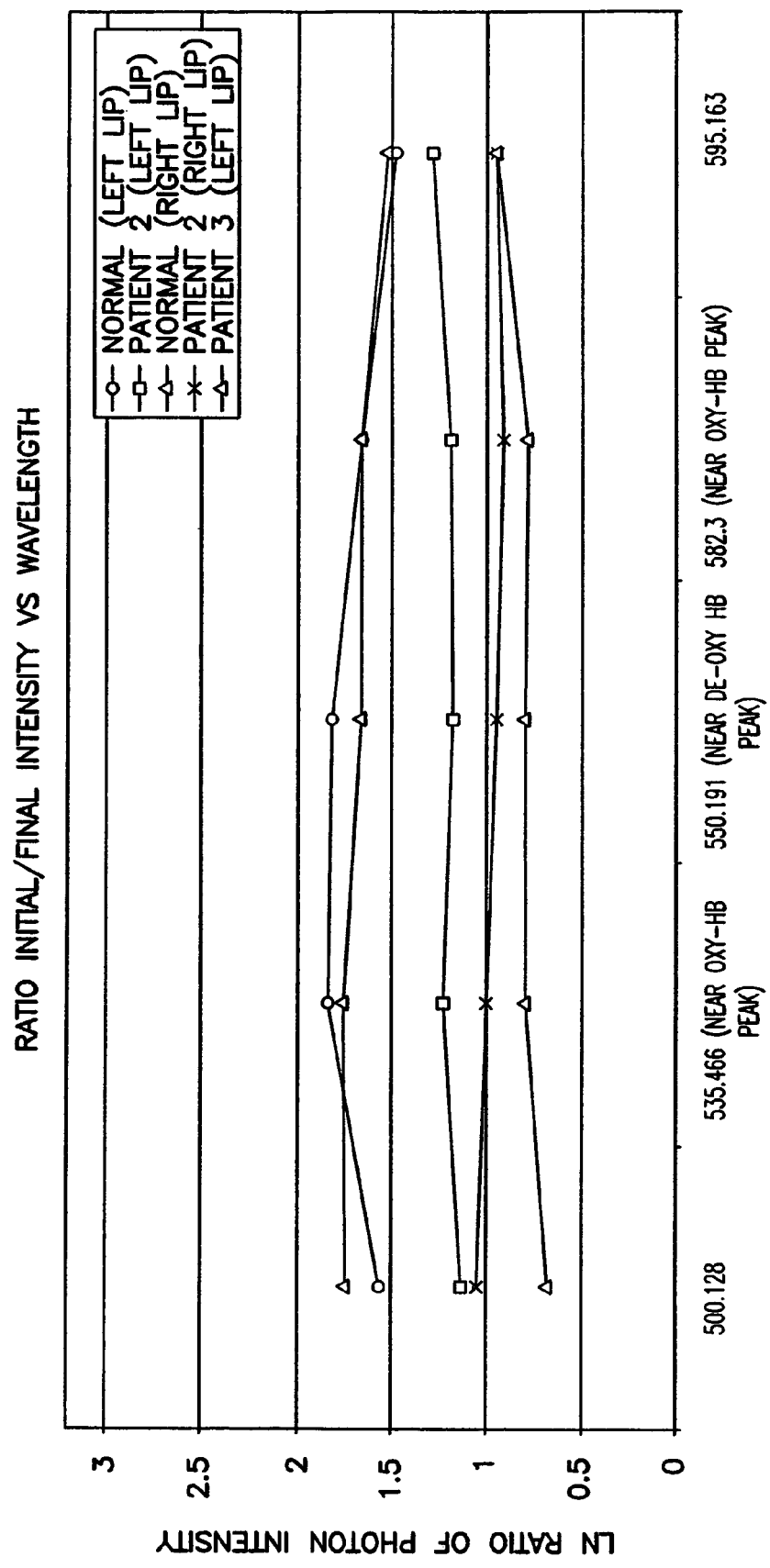
FIG. 13 is a graph that compares the left lip of a normal patient and a patient with a history of leukoplakia; and the right lip of a normal patient and two patients with history of leukoplakia.

Analysis of the logarithmic ratio of the intensity of the light from the 60° to the 30° source showed a maximum peak at a distance at or between detectors 2 and 3 in the sites that were from leukoplakia patients, FIG. 11. While the same graph for the control patient revealed no peak but rather a log—linear fall off, FIG. 12. The data from the patients are combined in FIG. 13. These trends are, qualitatively, in agreement with the theory plots. The peaks observed in the patients with leukoplakia are similar to the breakpoint in the theory plots; the peak is the point where the photon travels through the boundary between the epithelium and the stroma. The distance at which this peak occurs is directly related to the thickness of the epithelial layer. The reason that such a peak was not noted in the control patients' data is due to the fact that the epithelium in the non-smoking non-leukoplakia patients was not inflamed. Thus, the epithelial thickness is smaller and the transition point may be either undistinguishable or occur before the first source-detector separation distance. Additionally the value of the logarithmic ratio was between 0–5, which is in agreement with the theoretical data.

It is important to note that there was considerable variability of ratio value both between patients and between different sites on the same patient. Therefore one cannot make a generalization about the inflammation across the oral cavity, rather various sites must be measured and quantified. The degree of inflammation appears to vary amongst different sites within the patient and from patient to patient.

Monitoring of the location, specifically source to detector separation, at which the breakpoint occurs in the logarithmic ratio of intensity versus distance graphs, will enable an assessment of the trend in the inflammation of the epithelium and thereby the efficacy of leukoplakia treatments.

Working Example #2

Figure 14:
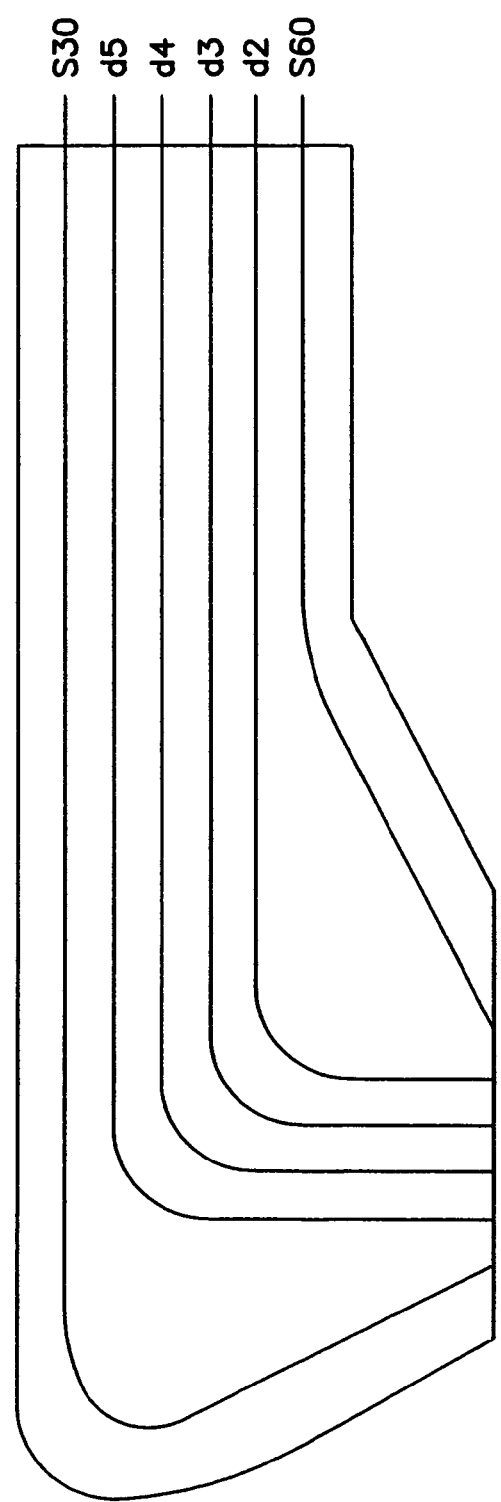
FIG. 14 is an illustration of one embodiment of a oral diffuse reflectance spectroscopy probe.

This example illustrates one method of detecting the boundary between the epithelium and stroma using a device and method of the invention. FIG. 14 depicts the probe used in this and the previous example with the detector and source fibers labeled. The optical wavelength resolution of the spectrometer used with the probe is 2 nm which spans approximately 6.3 charge coupled device (CCD) elements. Thus, the measurements oversample with respect to the optical characteristics of the device, in that measurements may be duplicative. This may be advantageous by allowing the intensities in adjacent positions to be averaged in order to reduce noise in the measurements. In this analysis, intensities of the 10 larger and smaller CCD elements are averaged so that intensity values used in the analysis cover a wavelength band of 6.35 $\mu$m, which is 3.2 times the fundamental resolution of the instrument.

Figure 15:
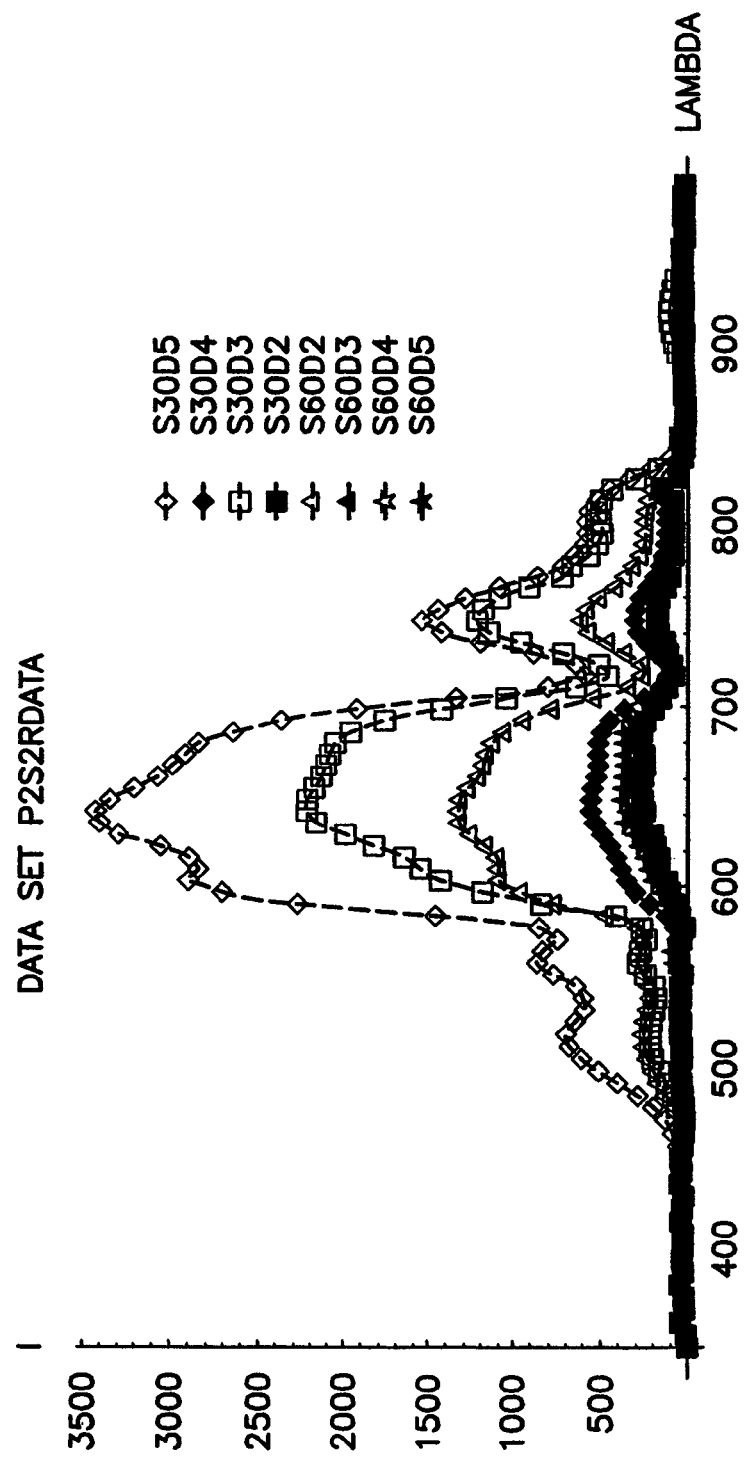
FIG. 15 depicts plots of raw data from an oral probe with eight different source-detector combinations.

The spectrum from each of eight source-pair combinations is shown in FIG. 15. To isolate the effect of the tissue, the filtering and effects of the source and transmission and detector fibers must be removed from the intensities measured by the spectrometer.

Due to manufacturing properties of the probe and fibers, each fiber has different light transmission characteristics. These different transmission characteristics are primarily due to coupling at the multiplexer and tissue interfaces. In order to isolate the effect of the tissues from these and other differences in transmission characteristics, it is necessary to mathematically remove these differences.

The measured fiber correction factors from the coupling at the multiplexer and tissue interfaces are shown in Table 2.

TABLE 2

|  | Fiber d2 | Fiber d3 | Fiber d4 | Fiber d5 |
|---|---|---|---|---|
| Raw Intensity | 2320 | 2400 | 2581 | 2469 |
| Normalized Efficiency | 0.899 | 0.930 | 1.000 | 0.957 |

This embodiment of the device of the invention has two source fibers that are connected to separate tungsten halogen lamps. A correction factor for the fiber transmission characteristics is also used to account for differences in intensity of the two lamps: it is assumed that the lamps are identical and differences in light reaching the tissue are due to the source fibers. The main cause of different intensities from the two source fibers is internal reflection at the end of the 60 degree source fiber due to the sharp angle at the tip of the fiber. The sharp angle of incidence reduces the light that enters the tissue empirically, $Is_{60}(\lambda)=0.88I_{S30}(\lambda)$ where $I_{S60}(\lambda)$ is the wavelength-dependent intensity at the end of the fiber connected to the 60-degree source and $I_{S30}(\lambda)$ is the wavelength-dependent intensity at the end of the fiber connected to the 30-degree light source.

The two source fibers in the probe are at opposite ends of the probe seen in FIG. 14. If the two sources were on the same side of the probe at exactly the same point, the distances to the detector fibers would be identical for each source. It is difficult to have the two sources at the same location, however, so the probe has the source fibers on opposite sides. Due to manufacturing tolerances for positioning the fibers, the distance from the S60 source to its nearest detector fiber is different from the distance from the S30 source to its nearest detector fiber. A correction must be applied before the ratio of these two measurements may be taken. Table 3 shows the position for each of the six fibers in the probe. As expected, it may be seen that the more angled source fiber, S60, has a larger span.

TABLE 3

| Point on Fiber | Fiber S60 (mm) | Fiber d2 (mm) | Fiber d3 (mm) | Fiber d4 (mm) | Fiber d5 (mm) | Fiber S30 (mm) |
|---|---|---|---|---|---|---|
| Inside Edge | 0.00 | 1.35 | 2.33 | 3.35 | 4.36 | 5.64 |
| Center | 0.30 | 1.55 | 2.59 | 3.55 | 4.59 | 6.03 |
| Outside Edge | 0.57 | 1.76 | 2.84 | 3.73 | 4.88 | 6.43 |

An exponential interpolation scheme was used to correct intensity measurements for the known source-detector distance errors.

$$I'(x,x')=e^{b(x-x')}I \quad (1)$$

where I is the measured intensity at point z and I' is the desired intensity value at point x'. The parameter b is obtained by fitting the known intensity data, I(x), to an exponential function before interpolation.

Given detector intensity measurements, the x position, or offset from the source, were obtained from the difference in source-detector positions using the center or edge positions given in Table 3. Initially, the center-to-center distances were used, but it was found that the nearest edge-to-edge distance was a better choice. This was because the intensity falls off exponentially with distance. The probability is highest that a detected photon was emitted from the edge of the source fiber that is closest to the detector and entered the detector on the edge closest to the source.

In the absence of any photons, the CCD has a small dark current that accumulates charge and results in a measured intensity. The measured intensity was a function of both the integration time of the CCD and the wavelength. Since the intensity values of the closest and farthest fiber may change by a factor of up to 100, the integration time of the CCD must be increased for measurements on the more distant fibers to obtain a signal that was significantly above the dark-current value, or dark count. This results in source-detector measurements at different integration times. To compare measurements made at different integration times, the dark count must be determined and subtracted from the measurements.

Figure 16:
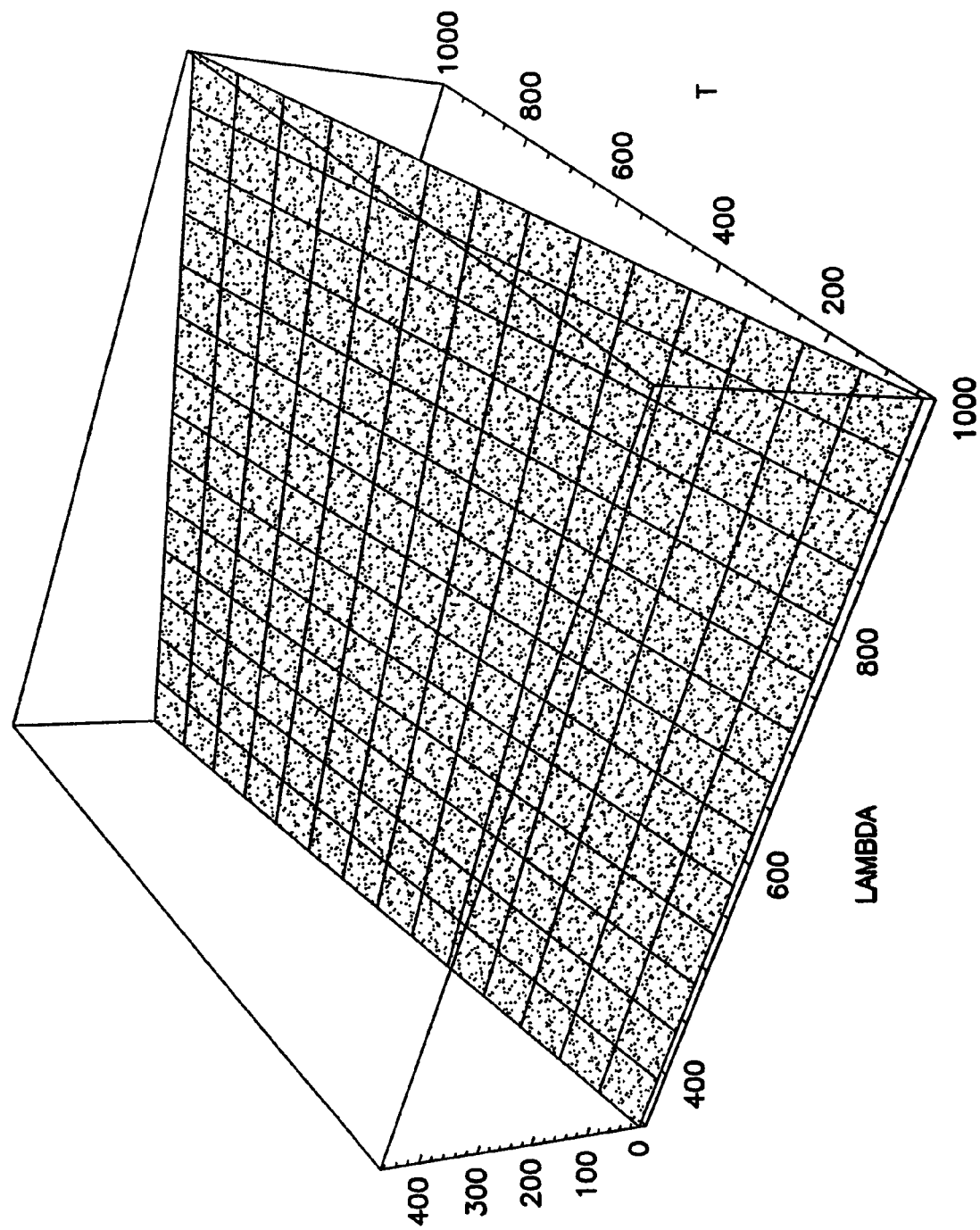
FIG. 16 is a graph of CCD intensity as a function of photon wavelength and integration time.

Dark counts for intensities at 2048 wavelengths were collected for several integration times. The data were fitted to a linear model, which resulted in the following relationship.

$$I_d=(\lambda,t_{int})=0.0004\lambda t_{int}+0.0537t_{int}+0.0041\lambda-4.2576 \quad (2)$$

where $\lambda$ is the wavelength in nanometers and $t_{int}$ is the CCD integration time in milliseconds. Typical values are plotted in FIG. 16.

Putting it all together, the intensity measured by the CCD from the 60 degree source may be written as follows.

$$I_{ccd,S60}(\lambda, t_{int}) = I_d(\lambda, t_{int}) + I_{S60}(\lambda) H_{S60fiber} pl_{S60,L1} H_{L1} pl_{S60,L2} H_{L2} H_{S60recfiber} \quad (3)$$

where $H_{S60fiber}$ characterizes the source fiber, $pl_{S60,L1}$ is the mean path-length in layer one of photons emitted by the 60 degree source, $pl_{S60,L2}$ is the mean path length in layer two of photons emitted by the 60 degree source, $H_{L1}$ and $H_{L2}$ characterize the optical properties of layer one and layer two respectively and $H_{S60recfiber}$ characterizes the optical properties of the receiver/detector fiber which carries the photons to the spectrometer.

Figure 17:
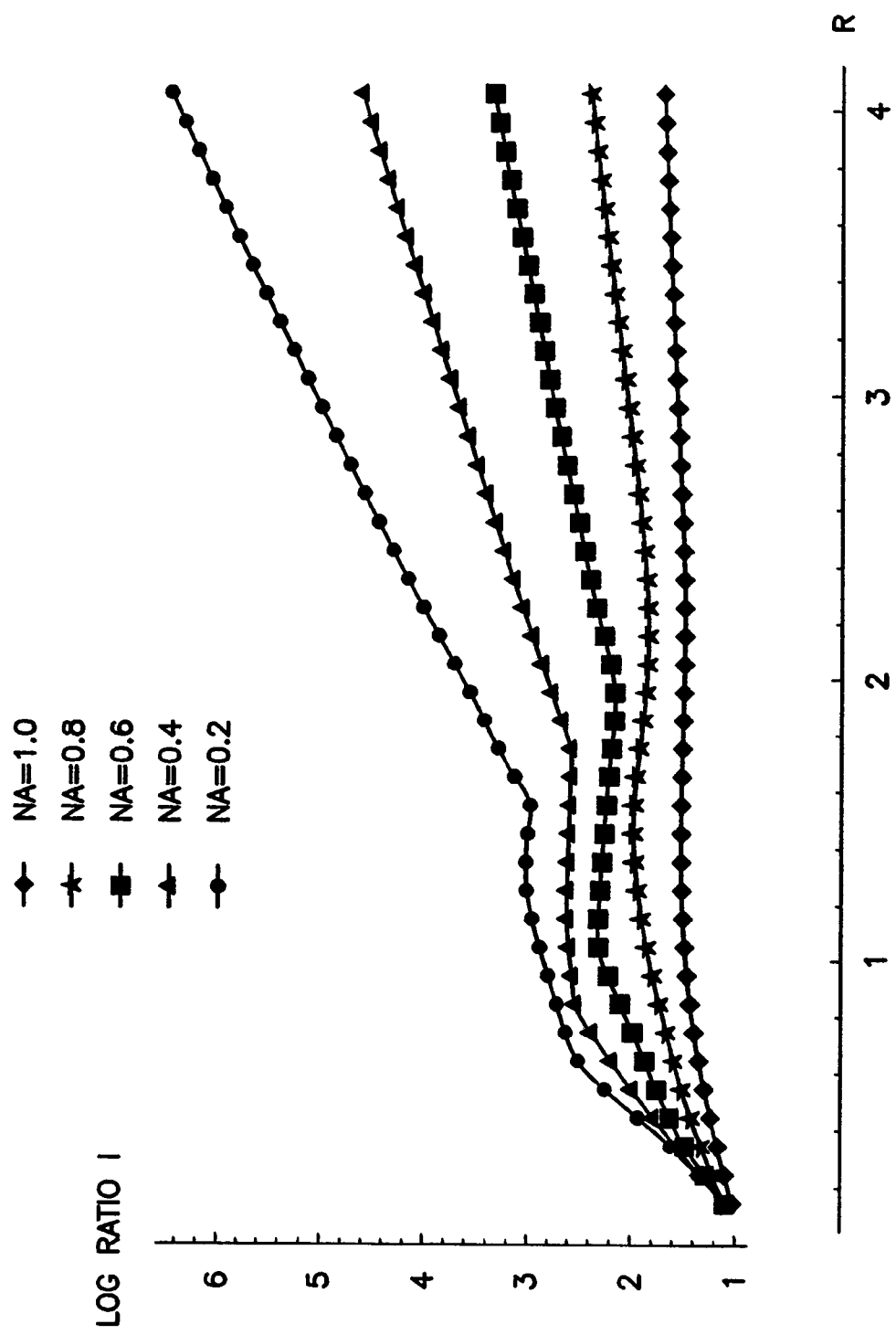
FIG. 17 is a graph of the log of the ratio of the intensities for different detector numerical apertures.

The ratios plotted in FIG. 17 are:

$$I_{S60/S30}(\lambda, t_{int}) = \frac{pl_{S60,L1} H_{L1} pl_{S60,L2} H_{L2}}{pl_{S30,L1} H_{L1} pl_{S30,L2} H_{L2}} \quad (4)$$

where $pl_{S30,L1}$ and $pl_{S30,L2}$ are mean path-lengths in layer one and layer two for photons emitted by the 30 degree source. To convert the measured data as expressed in Eq. 3 to the form in Eq. 4, first the dark-count, $I_d$ must be subtracted from the raw measurements. Occasionally, subtracting the dark-count will result in a negative value. Since the CCD output can never be negative, negative values are not allowed and zero is used instead. As stated before, it is assumed that the two source intensities are the same with any actual differences contained in the respective source-fiber H term. Correcting also for the different fiber characteristics yields $$I_{S60/S30}(\lambda, t_{int}) = \frac{(I_{ccd,S60} - I_d(\lambda, t_{int})) H_{S30\ fiber} H_{S30recfiber}}{(I_{ccd,S60} - I_d(\lambda, t_{int})) H_{S60\ fiber} H_{S60recfiber}} \quad (5)$$

where $H_{S30fiber}$ characterizes the 30 degree source fiber and $H_{S30recfiber}$ is for the different detector fiber used with the 30 degree source. Empirically, the ratio $$\frac{H_{S30\ fiber}}{H_{S60\ fiber}} = 1/0.88$$

as stated above. The ratio $$\frac{H_{S30recfiber}}{H_{S60recfiber}}$$

accounts for different coupling efficiencies and manufacturing errors in fiber position. Using the values given in Table 2 and 3 with Eq. 1 one gives the values in Table 4.

Figure 18:
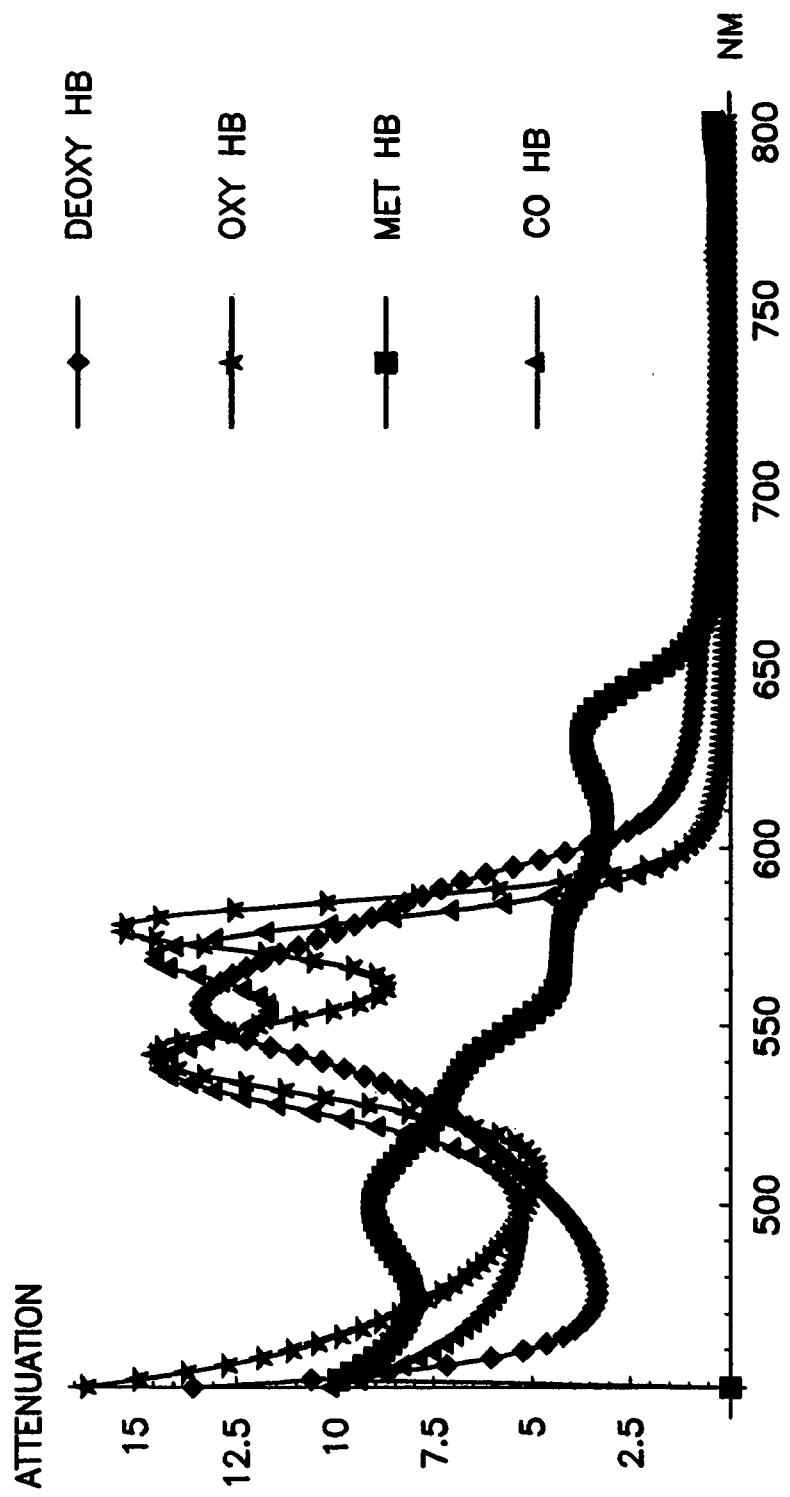
FIG. 18 is a graph depicting the absorption of different types of hemoglobin at variable wavelengths.

The underlying theory requires that absorption be on the order of the same magnitude as scattering. For this to occur in tissue requires the use of a wavelength with high absorption. Hemoglobin provides such high absorption for wavelengths between 500 nm and 600 nm as may be seen in FIG. 18.

Figure 19:
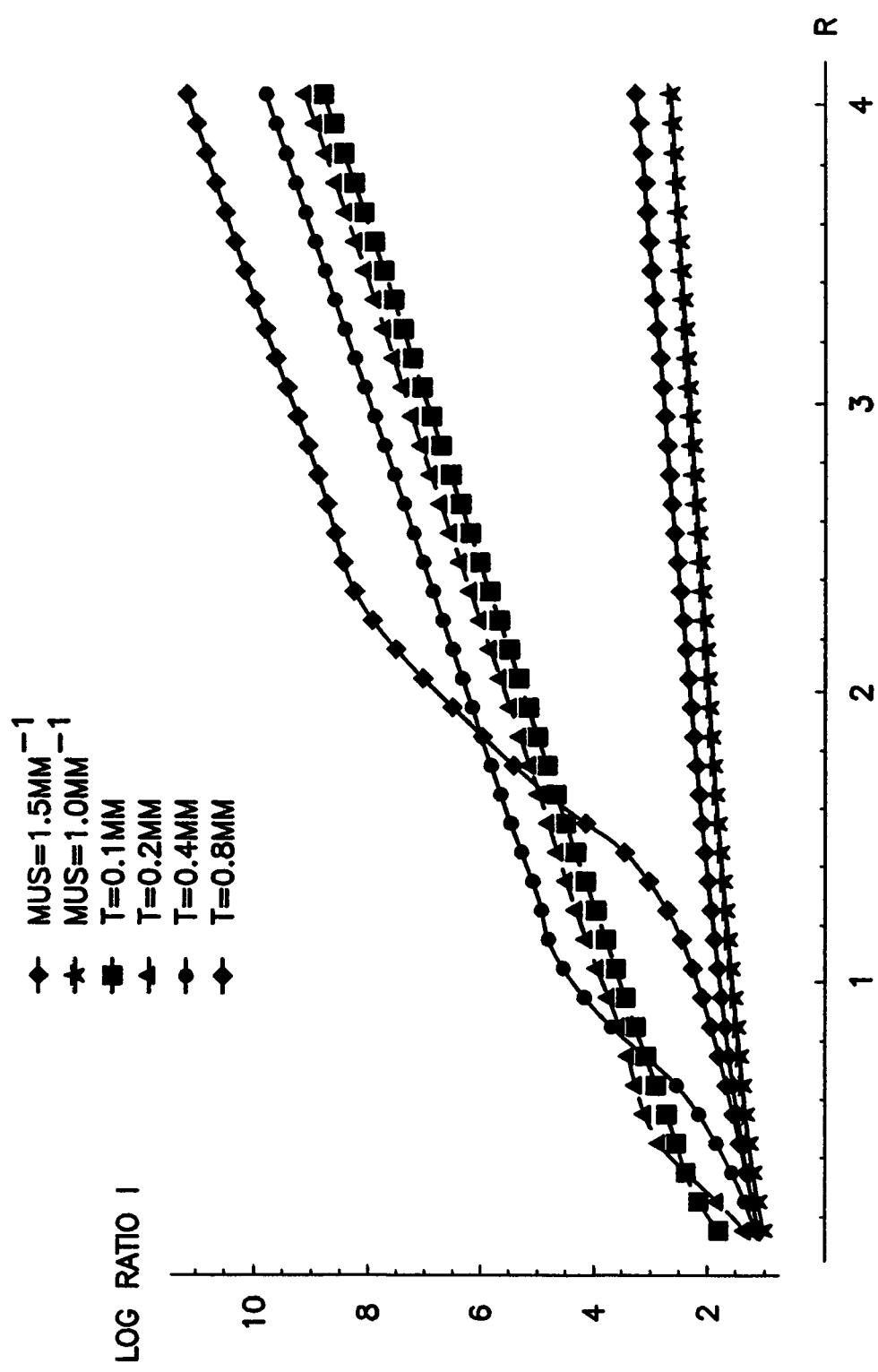
FIG. 19 is a graph depicting the log of the intensity ratio for layers of differing thicknesses.

Since the probe only measures four spatially resolved positions, it was not possible to quantify thickness by matching to the plots shown in FIG. 19 (which represents theoretical optical coefficients closest to those expected in patients). For the clinical work, a simple feature that indicated an approximate level of inflammation was desired. As may be seen in FIG. 19, the greater the inflammation, the greater the intensity ratio becomes at an offset of 3.8 mm which corresponds to the outermost probe fiber. Further, the greater the inflammation, the smaller the intensity ratio at an offset corresponding to the innermost probe fiber of approximately 0.77 mm. Thus, the ratio of the intensity ratio of the outer point over the inner point will be smaller for healthy patients and larger for inflamed tissue.

From the foregoing detailed description, the invention has been described in a preferred embodiment. Modifications and equivalents of the disclosed concepts are intended to be included within the scope of the appended claims.

What is claimed is:

1. A device for measuring the thickness of the epithelium layer, the device comprising:
   a handle; a head; and an optical fiber bundle,
   wherein said optical fiber bundle is contained within said handle and said head, and said handle is connected to said head,
   wherein said head comprises a contact area that defines a normal, wherein said normal is an axis that is at a 90° angle from said contact area,
   wherein said optical fiber bundle comprises a source and a detector, said source comprising first and second respective optical fibers, said first optical fiber positioned at a first angle relative to said normal and said second optical fiber positioned at a second angle relative to said normal wherein said first and second angles are different, and
   wherein said optical fiber bundle ends at said contact area of said head.

2. The device of claim 1, wherein said optical fiber bundle comprises at least four individual fibers.

3. The device of claim 2, wherein said individual fibers have an outer diameter less than or equal to about 0.25 mm, with a core diameter less than or equal to 240 Tm.

4. The device of claim 2, wherein said individual fibers are polymeric.

5. The device of claim 4, wherein said fibers result from the reaction of more than one monomeric precursor.

6. The device of claim 2, wherein said individual fibers are aligned.

7. The device of claim 1, wherein the optical fiber bundle comprises at least six individual fibers.

8. The device of claim 1, wherein the first and second angles are 30° and 60° from normal.

9. The device of claim 1, wherein said optical fiber bundle consists of at least nine individual optical fibers.

10. The device of claim 9, wherein three of said individual fibers are utilized as a source of energy, and six of said individual fibers are utilized as detectors of energy.

11. The device of clam 10, wherein said three individual fibers utilized as a source of energy are configured so as to be at angles of 60°, 45° and 0° from normal.

12. The device of claim 11, wherein said three individual fibers are fused together using a transparent optical epoxy.

13. The device of claim 1, wherein said device consists of at least two separate pieces joined as to allow movement about the joined region.

14. The device of claim 1 additionally comprising an external light source, and an external multiplexer.

15. The device of claim 1 additionally comprising an external light source, an external multiplexer, an external spectrometer, and an external computer system.

16. The device of claim 1 additionally comprising at least one internal light source.

17. The device of claim 16 additionally comprising an internal multiplexer.

18. The device of claim 17 additionally comprising an internal microprocessor.

19. A device for measuring the thickness of the epithelium layer, the device comprising an image conduit; at least a first and a second source fiber, and a head, wherein said image conduit and said at least first and second source fibers are contained within said head, wherein said head comprises a contact area that defines a normal, wherein said normal is an axis that is at a 90° angle from said contact area, wherein said first source fiber is positioned at a first angle relative to said normal and said second optical fiber positioned at a second angle relative to said normal, and wherein said first and second angles are different.

20. The device of claim 19, wherein said image conduit is a high resolution fiber image conduit.

21. The device of claim 20, wherein said high resolution fiber image conduit has resolution of at least 12 µm.

22. The device of claim 20, wherein said high resolution fiber image conduit has a diameter of at least 3.2 mm.

23. The device of claim 19, further comprising at least one other optical fiber configured as a third source of light.

24. The device of claim 23, wherein said two other optical fibers are at angles of 0° and 45° to normal.

* * * * *